United States Patent [19]

Gupta

[11] Patent Number: 5,288,865
[45] Date of Patent: Feb. 22, 1994

[54] PROCESS FOR PREPARING AMIDE DERIVATIVES FROM HALOAMINOTRIAZINES AND ACID HALIDES

[75] Inventor: Ram B. Gupta, Bronx, N.Y.

[73] Assignee: American Cyanamid Company, Stamford, Conn.

[21] Appl. No.: 968,871

[22] Filed: Oct. 30, 1992

Related U.S. Application Data

[63] Continuation-in-part of Ser. No. 793,077, Nov. 15, 1991, abandoned.

[51] Int. Cl.$^5$ .................. C07D 251/54; C07D 413/04
[52] U.S. Cl. ................................. 544/200; 544/113; 544/197; 544/198; 544/205; 544/206; 544/207; 544/214
[58] Field of Search ............... 544/113, 197, 200, 198, 544/205, 206, 207, 214

[56] References Cited

U.S. PATENT DOCUMENTS

| | | | |
|---|---|---|---|
| 2,184,883 | 12/1939 | Muskat et al. | 23/190 |
| 2,184,886 | 12/1939 | Muskat et al. | 260/248 |
| 2,184,888 | 12/1939 | Muskat et al. | 23/90 |
| 2,472,361 | 6/1949 | Arsem | 260/583 |
| 2,507,700 | 5/1950 | Emerson et al. | 260/249.5 |
| 2,577,418 | 12/1951 | Hamm | 260/97.5 |
| 3,291,763 | 12/1966 | Becalick et al. | 260/13 |
| 3,743,642 | 7/1973 | Schwarzmann et al. | 260/249.6 |
| 3,920,832 | 11/1975 | Barer et al. | 424/300 |
| 4,732,899 | 3/1988 | Gehret et al. | 514/245 |
| 4,824,845 | 4/1989 | Gehret et al. | 514/245 |
| 4,939,213 | 7/1990 | Jacobs et al. | 525/329.9 |
| 5,084,541 | 1/1992 | Jacobs et al. | 528/45 |

FOREIGN PATENT DOCUMENTS

| | | |
|---|---|---|
| 239121 | 9/1987 | European Pat. Off. |
| 58-146582 | 9/1983 | Japan |
| 663546 | 6/1967 | South Africa |

OTHER PUBLICATIONS

Pinchuk et al, Chemical Abstract, vol. 75, #129306g 1971.

U. von Gizycki, *Isocyanato-s-Triazines*, Angewandte Chemie, International ed., vol. 10, p. 403 (1971).
H. Kitajima, T. Imanaka, T. Yamamoto, Chem. Abstracts vol. 82, No. 11, 72946d (1975).
A. M. Pinchuk, T. V. Kovalevskaya, G. K. Bespal'ko, Chem. Abstracts, vol. 75 (21), item 129306g (1971).
Zhurnal Organicheskoi Khimi, vol. 7, No. 7, p. 1541, Jul., 1971 and published translation.
L. I. Samarai, V. P. Belayer, G. F. Galenko, and G. I. Derkach, Chem Abstracts, vol. 72 (17), item 90006v (1970).
L. I. Samarai, V. P. Belayer, G. F. Galenko, and G. I. Derkach, Zhurnal Organicheskoi Khimii, vol. 6, No. 1, pp. 85-88, Jan. 1, 1970, published translation.
E. M. Smolin and L. Rapoport, "S-Triazines and Derivatives," Interscience Publishers Inc., New York, p. 333 (1959).
B. Bann and S. A. Miller, "Melamine and Derivatives of Melamine," Chem. Revs., vol. 58, pp. 131-172 (1958).
A. Ostrogovich, Chem Abstracts, vol. 30, p. 465 (1936).
M. J. Coghlan and B. A. Caley, "Trichloromethyl Carbonate as Practical Phosgene Source," Tetrahedron Letters, vol. 30, No. 16, pp. 2033-2036 (1989).

*Primary Examiner*—Cecilia Tsang
*Assistant Examiner*—Y. N. Gupta
*Attorney, Agent, or Firm*—Bart E. Lerman; Frank M. Van Riet; Michael J. Kelly

[57] ABSTRACT

This invention provides a process for preparing amide derivatives of acids by the reaction of haloaminotriazines and acid halides.

This invention also provides a process for preparing isocyanates and isocyanate adducts from amide derivatives derived from haloaminotriazines and acid halides such as oxalyl chloride, phosgene and phosgene analogs.

Melamine derived acid amides are prepared by reaction of trichloro and hexachloromelamines with chloroformates and acid chlorides. The by-product chlorine may be recycled in this process.

Amides, carbamates, sulfonamides, phosphoramides, and related amide derivatives may be prepared by the novel processes of the invention.

13 Claims, 2 Drawing Sheets

PROCESS FOR PREPARING AMIDE DERIVATIVES FROM HALOAMINOTRIAZINES AND ACID HALIDES

CROSS-REFERENCE TO RELATED APPLICATION

This application is a continuation-in-part of U.S. application Ser. No. 07/793,077, filed Nov. 15, 1991 now abandoned.

BACKGROUND OF THE INVENTION

1. Field of the Invention

This invention relates to the preparation of amide derivatives of acids by a novel reaction which combines the amino group of a haloaminotriazine with the non-halide portion of an acid halide. The reaction also combines the halogen atom of said haloaminotriazine with the halogen atom of the acid halide producing a halogen molecule as a by-product. This invention is also directed to a novel process of preparing isocyanates and isocyanate adducts from haloaminotriazines and selected acid halides.

2. Related Background Art

Amides can be prepared by the reaction of amines with acid halides. Although the reaction of amines with acid chlorides is quite general, it is sluggish and often fails to take place if the amine is deactivated by the presence of at least one electron withdrawing substituent. In some cases, preparation of an amide may be possible by first deprotonating the amine with a strong base to generate an anion and then allowing the amine to react with the acid halide. This approach, however, is often impractical, costly, and very limited in scope, and is inoperative if the amine has low solubility, high molecular weight, or both.

Triazine tris-carbamates have been prepared by converting an aminotriazine to an isocyanate group, by reacting the aminotriazine with oxalyl chloride, followed by reaction with an alcohol. This two step approach is described in U.S. Pat. Nos. 4,939,213 and 5,084,541. The patents also describe curable compositions using triazine tris-carbamates. The preparation of other carbamates by the above mentioned approach is described in an article by U. Von Gizycki in Angewandte Chemie, International edition, Volume 10, page 403, (1971), entitled "Isocyanato-s-Triazines." The author states therein that until that time, only one isocyanato-s-triazine, namely the 2,4-dichloro-6-isocyanate, derivative had previously been isolated, and that from tetrameric cyanogen chloride by a route that cannot be generalized.

Partially successful attempts to prepare mono- and bis-carbamates from aminotriazines and haloformates are described in an article entitled "Melamine Derivatives 18: Reactions of Melamine and Benzoguanamine with Ethyl Chlorocarbonate" by H. Kitajima, T. Imanaka, and T. Yamomoto in Yuki Gosei Kagaku Kyokai Shi, Volume 32, Number 9, pages 723 to 726 (1974); Chemical Abstracts Volume 82, Number 11:72946d. The article, however, does not mention the preparation of tris-carbamates.

Preparation of halomelamines are disclosed in U.S. Pat. Nos. 2,184,888; 2,184,886; 2,184,883; 3,743,642; and 2,472,361; in South African Patent No. 66-03546; and in European Patent No. 239,121. The reaction of oxalyl chloride with N,N-dichloroalkylamines or N,N-dichloroamides, to form N-chloro-N-alkyloxamyl chlorides or isocyanates, is disclosed in Chemical Abstracts, Vol. 75 (21), item 129306 g, condensed from a Russian Language article in Zh. Org. Khim., Vol. 7, No. 7, p. 1541 (1971). The reaction of N-chlorocarboximidic esters with oxalyl chloride is disclosed in Chemical Abstracts, Vol. 72 (17), item 90006v, condensed from a Russian Language article in Zh. Org. Khim., Vol. 6, No. 1, p. 85–88 (1970).

It is well known that the chemistry of amines and triazines is quite different. In a publication by E. M. Smolin and L. Rapaport entitled "S-Triazines and Derivatives", Interscience Publishers Inc., New York, page 333 (1959), it is reported that attempts to react an acid halide with the amino group on a triazine such as melamine have not been successful. Likewise, the reaction of melamine with alkyl halides, such as allyl chloride, is known to result in alkyl substitution at the nitrogen on the triazine ring resulting in isomelamine derivatives.

Melamine chemistry, particularly halomelamine chemistry including preparation and applications, is discussed in an article by B. Bann and S. A. Miller entitled "Melamine and Derivatives of Melamine", Chemical Reviews, Volume 58, pages 131 to 172, (1958). It is stated therein on page 148 that acyl halides such as benzoyl chloride in the Schotten-Baumann reaction have no effect on melamine. The inertness of melamine towards acid halides is further described in Chemical Abstracts Vol. 30, p. 465 (1936) and in U.S. Pat. No. 2,557,418.

In view of the reported difficulties encountered by practitioners in the fields of melamine and aminotriazine chemistry, a novel chemical reaction which overcomes the aforementioned difficulties and provides a general method for preparing acylated aminotriazines from widely available haloaminotriazine precursors would be a valuable addition to the very limited methods available to date. When not commercially available, the haloaminotriazines are easily prepared by well known methods.

It is the object of this invention to provide a simple process for preparing amides from haloaminotriazines and acid halides.

It is also an object of this invention to provide a process for preparing isocyanates starting from haloaminotriazines and acid halides Another object of this invention is to provide a process for preparing isocyanate adducts starting from haloaminotriazines and acid halides.

This invention involves a novel chemical reaction which combines the amine group of a haloaminotriazine with the non-halide portion of an acid halide to produce an acid amide and recyclable halogen. The preparation of isocyanates is accomplished by decomposing specific acid aides to the isocyanates and the isocyanate adducts are then prepared by reacting the isocyanates with active hydrogen-containing compounds.

SUMMARY OF THE INVENTION

This invention provides a process for preparing amide derivatives of acids from haloaminotriazines and acid halides.

The amides are prepared by a reaction which combines the amino group of the haloaminotriazine with the non-halide portion of the acid halide. Concurrently, the novel reaction also combines the halogen atom of said haloaminotriazine with the halogen atom of said acid halide producing a halogen molecule as a recyclable by-product. This invention also provides a process for preparing isocyanates and isocyanate adducts starting from haloaminotriazines and certain acid halides, which comprises decomposing select acid amides to an isocyanate and further reacting the isocyanate with an active hydrogen-containing compound to form an isocyanate adduct.

The processes of the invention have many advantages some of which are described hereinbelow. For example, these processes afford products which are characterized by low salt, low color, high purity, and high yield. The processes are also applicable for use with acid or base sensitive substrates, and are carried out in a neutral medium. Most importantly, the invention allows facile functionalization and isolation of aminotriazine derivatives such as melamine and benzoguanamine without the use of formaldehyde. Another advantage of the invention described herein is that it allows the facile functionalization of insoluble amines such as melamine by a simple halogenation, acylation, and dehalogenation cycle. The processes of the invention may also be employed with specific acid halides, such as oxalyl chloride or phosgene, so as to provide a process for the preparation of isocyanates and isocyanate adducts, particularly those of aminotriazines.

The invention also provides novel products prepared by the processes of the invention.

DETAILED DESCRIPTION OF THE INVENTION

Figure 1:
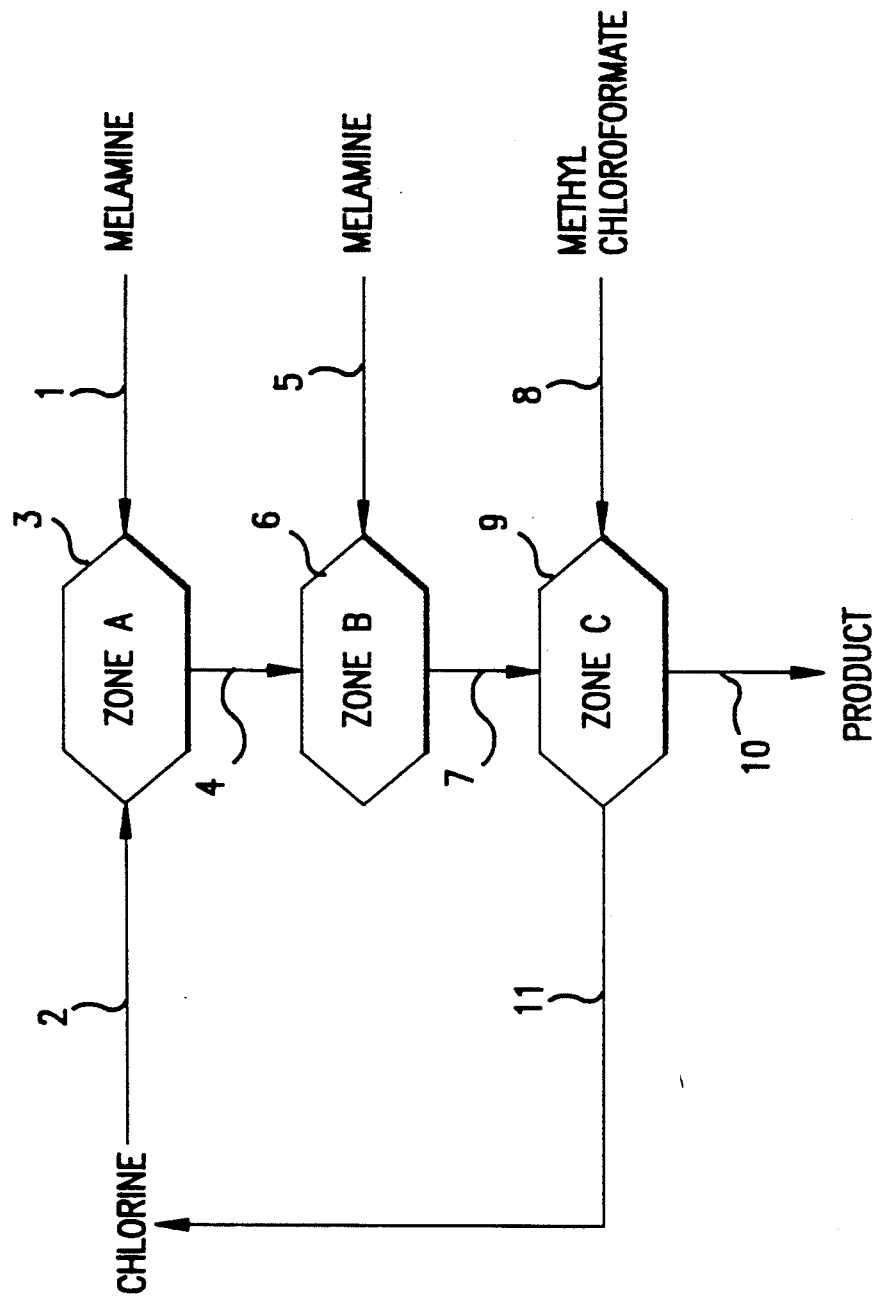
FIG. 1 schematically illustrates a process for producing triazine tris-methyl carbamate from melamine via trichloromelamine.

This invention is a novel process for preparing certain acid amides from a haloaminotriazine and an acid halide, comprising the step of contacting said haloaminotriazine with said acid halide at a temperature and for a length of time sufficient to produce said acid amide as a product, and halogen as a by-product.

The term "acid halide" herein refers to a derivative of weak or strong hydroxylic acids wherein the hydroxy group is converted to a halogen. An example of an acid halide usable in this invention is acetyl chloride, which may be derived from acetic acid by converting the acid hydroxy group to chloride by a suitable reagent. Any acid halide can be employed in this invention.

The term "acid amide" is used in the context of this invention to denote products derived from acid halides by a simple replacement of the halide atoms thereof with an amino group of a haloaminotriazine. Furthermore, in the context of this invention, a carbamate may be viewed to be an "acid amide" as defined herein, because a carbamate may be derived from a halo-formate by replacement of the halide with an amino group.

The term "haloaminotriazine" is defined herein as an aminotriazine compound in which at least one amino nitrogen-bound hydrogen is replaced by a halogen atom.

The acid halide and haloaminotriazine reactants and the acid amides resulting from the novel reaction thereof are described in greater detail below.

THE NOVEL REACTION

The reaction of amines with acid halides is known and may be exemplified by Equation (1):

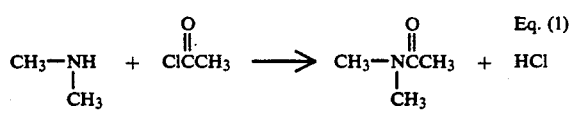

While it is known that amides and amines are readily N-acylated with acyl halides, it is also known, as discussed above, that triazines such as melamine are not N-acylated by acyl halides. Surprisingly, however, I have found that a novel, hitherto unreported reaction takes place between haloaminotriazines and an acid halide. The novel reaction is exemplified by Equation (2):

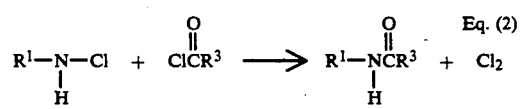

wherein $R^1$ is a triazine nucleus and wherein $R^3$ is a substituent on the acid halide. The substitution of the haloaminotriazine at the amino halide in the novel reaction, instead of at the amino proton, is completely unexpected based on well known amine chemistry. The novel reaction will also occur if the amino hydrogen is replaced by halogen or another substituent.

Reactions according to Equation (2), and other analogous amide.forming reactions of haloaminotriazines and acid halides, are referred to herein as "the novel reaction of the invention."

THE HALOAMINOTRIAZINES

The haloaminotriazines usable in this invention are aminotriazine compounds wherein at least one nitrogen bound hydrogen is replaced by a halogen atom.

The amine precursors of the haloaminotriazines of the invention may be monomeric or polymeric. They may be very soluble or sparingly soluble in organic solvents. Even haloaminotriazines which are derived from amine precursors that have solubilities less than 10 weight percent in organic solvents, particularly in halogenated organic solvents, are useful.

The haloaminotriazines usable in the process of this invention may be represented by the following formula (1):

[1]

wherein L is at least 1; and when L is at least 2, each

group is the same or different;

X is a halogen selected from the group consisting of chloro, bromo, iodo, and fluoro groups and mixtures thereof;

B is selected from the group consisting of hydrogen, chloro, bromo, iodo, fluoro, alkyl, alkylenealkoxy, triazino, pyrimidino, pyridino, imidazolo, tetrazolo, silyl, cyano, perfluoroalkyl, perfluoroaryl, and perfluoroaralkyl groups, and mixtures thereof;

A is an L-functional anchor selected from the group consisting of triazines represented by the following formulae [2] and [3]:

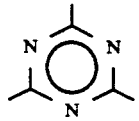
[2]

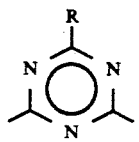
[3]

wherein R is selected from the group consisting of linear alkyl of 1 to 20 carbon atoms, cyclic or branched alkyl of 3 to 20 carbon atoms, alkenyl of 2 to 20 carbon atoms, aryl of 6 to 20 carbon atoms, aralkyl of 7 to 20 carbon atoms, alkoxy of 1 to 20 carbon atoms, aryloxy of 6 to 20 carbon atoms, alkylthio of 1 to 20 carbon atoms, arylthio of 6 to 20 carbon atoms, alkylamino of 1 to 20 carbon atoms, dialkylamino of 2 to 40 carbon atoms, morpholino, piperidino, pyrrolidino, aminotriazino, alkylaminotriazino, aminoalkylaminotriazino, hydrogen, chloro, bromo, iodo, fluoro, perfluoroalkyl, perfluoroaryl, and perfluoroaralkyl groups.

Mixtures of any of the above described haloaminotriazines may be employed in the processes of this invention.

When A in formula [1] above is a triazine nucleus represented by formula [2] above, the resulting haloaminotriazine is a halomelamine represented by the following formula [4]:

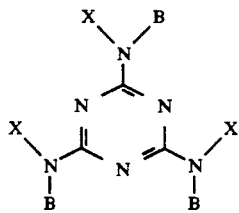
[4]

wherein each X group is the same or different and is selected from the group consisting of hydrogen, chloro, bromo, iodo and fluoro groups, provided that at least one X group is a halogen; and wherein each B group is the same or different and is selected from the group consisting of hydrogen, chloro, bromo, iodo, fluoro, triazino, pyrimidino, pyridino, imidazolo, tetrazolo, silyl, cyano, perfluoroalkyl, perfluoroaryl, and perfluoroaralkyl groups.

By way of example, the haloaminotriazines include monohalomelamine, dihalomelamine, trihalomelamine, tetrahalomelamine, pentahalomelamine, hexahalomelamine, isomers thereof, and mixtures thereof. The preferred halogen in the haloaminotriazine is chloride.

The preferred haloaminotriazines are the chloromelamines. The most preferred chloromelamines are hexachloromelamine and N,N',N''-trichloromelamine isomers represented by the formulae:

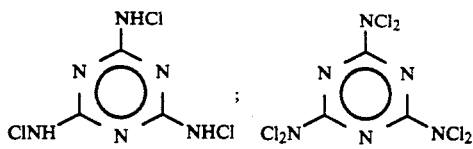

N,N',N''-trichloromelamine (also known as N,N',N''-trichloro-2,4,6-triamino-1,3,5-triazine) is commercially available from Aldrich Chemical Company, Milwaukee, Wis., as an off white powder. The preparation of mono-, di-, tri-, and hexa-chloromelamine, and bromo- and iodo-melamines is reviewed in pages 159 to 162 of the article by B. Bann and S. A. Miller cited previously hereinabove and is further described in U.S. Pat. No. 2,472,361 in detail.

When A in formula [1] above is a triazine nucleus represented by formula [3] above, the resulting haloaminotriazine is a haloguanamine represented by the following formula [5]:

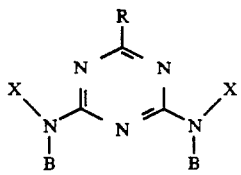
[5]

wherein X and B are the same as defined above for formula [4]; and wherein R is selected from the group consisting of linear alkyl of 1 to 20 carbon atoms, cyclic or branched alkyl of 3 to 20 carbon atoms, alkenyl of 2 to 20 carbon atoms, aryl of 6 to 20 carbon atoms, aralkyl of 7 to 20 carbon atoms, alkoxy of 1 to 20 carbon atoms, aryloxy of 6 to 20 carbon atoms, alkylthio of 1 to 20 carbon atoms, arylthio of 6 to 20 carbon atoms, alkylamino of 1 to 20 carbon atoms, dialkyl amino of 2 to 40 carbon atoms, morpholino, piperidino, pyrrolidino, aminotriazino, alkylaminotriazino, aminoalkylaminotriazino, hydrogen, chloro, bromo, iodo, fluoro, prefluoroalkyl, perfluoroaryl, and perfluoroaralkyl groups.

Haloguanamines are also among the preferred haloaminotriazines of the invention and include N-substituted mono-, di-, tri-, and tetra- halo acetoguanamines, cyclohexyl-carboguanamines and benzoguanamines. Particularly preferred are the haloguanamines where the halogen is chloride.

THE ACID HALIDES

By way of example, the acid halides usable in the practice of this invention may be represented generically by the formula:

wherein M is at least 1; and when M is at least 2, each $\text{(Y—X)}$ group is the same or different;

X is a halogen selected from the group consisting of chloro, bromo, iodo, and fluoro groups, and mixtures thereof;

Y in each $\text{(Y—X)}$ group is the same or different and each is selected independently from the group consisting of the following functionialities represented by the formulae:

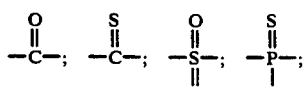

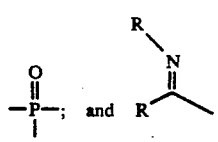

wherein each R is independently an alkyl, aryl, or an alkoxy group; and

Z is an M-functional anchor selected from the group consisting of hydrogen, chloro, bromo, iodo, fluoro, vinyl, alkyl of 1 to 20 carbon atoms, alkylene of 1 to 20 carbon atoms, arylene of 6 to 20 carbon atoms, haloalkyl of 1 to 20 carbon atoms, aryl of 6 to 20 carbon atoms, haloaryl of 6 to 20 carbon atoms, aralkyl or 7 to 20 carbon atoms, haloaralkyl of 7 to 20 carbon atoms, acyl of 2 to 20 carbon atoms, haloacyl of 2 to 20 carbon atoms, halocarbonyl, alkoxycarbonyl of 2 to 20 carbon atoms, alkylthiocarbonyl of 2 to 20 carbon atoms, haloalkoxy of 2 to 20 carbon atoms, aminocarbonyl, alkylaminocarbonyl of 2 to 20 carbon atoms, dialkylaminocarbonyl of 3 to 20 carbon atoms, alkenylaminocarbonyl of 4 to 20 carbon atoms, dialkenylaminocarbonyl of 7 to 40 carbon atoms, alkylalkenylaminocarbonyl of 5 to 20 carbon atoms, triazino, pyrimidino, pyridino, imidazolo, tetrazole, perfluoroalkyl of 1 to 20 carbon atoms, perfluoroaryl of 6 to 20 carbon atoms, perfluoro aralkyl of 7 to 20 carbon atoms, alkoxycarbonylalkyl of 3 to 20 carbon atoms, cyanoalkyl of 2 to 20 carbon atoms, formylalkyl of 2 to 20 carbon atoms, ketoalkyl of 3 to 20 carbon atoms, trialkoxysilylalkyl of 4 to 20 carbon atoms, dialkylaminoalkyl of 3 to 20 carbon atoms, alkoxyalkyl of 2 to 20 carbon atoms, alkoxy of 1 to 20 carbon atoms, aryloxy of 6 to 20 carbon atoms, alkenyloxy of 3 to 20 carbon atoms, alkylenedioxy of 2 to 20 carbon atoms, arylenedioxy of 6 to 20 carbon atoms, N,N-dialkylamino of 2 to 40 carbon atoms, N,N-dialkenylamino of 6 to 40 carbon atoms, N,N-diarylamino of 12 to 40 carbon atoms, N,N-alkylalkenylamino of 4 to 20 carbon atoms, N,N-alkylarylamino of 7 to 20 carbon atoms, N,N-alkenylarylamino of 9 to 20 carbon atoms, aziridino, azetidino, pyrrolidino, piperidino, morpholino, alkylmercapto of 1 to 20 carbon atoms, alkenylmercapto of 3 to 20 carbon atoms, and arylmercapto of 6 to 20 carbon atoms.

The preferred halogen group is chloro, the preferred Y group is a carbonyl group, and the preferred anchor Z group is selected from alkyl, haloalkyl, and alkoxy groups.

Among the preferred acid halides suitable for use in the practice of the invention are the following classes:
alkyl chloroformates
aryl chloroformates
acyl chlorides
haloalkylcarbonyl chlorides
acryloyl chlorides
carbamoyl chlorides
alkylene bis acid chlorides
arylene bis acid chlorides
alkylene bis chloroformates, and phosgene.

Specific examples of acid halides usable in this invention are the following compounds represented by the formulae:

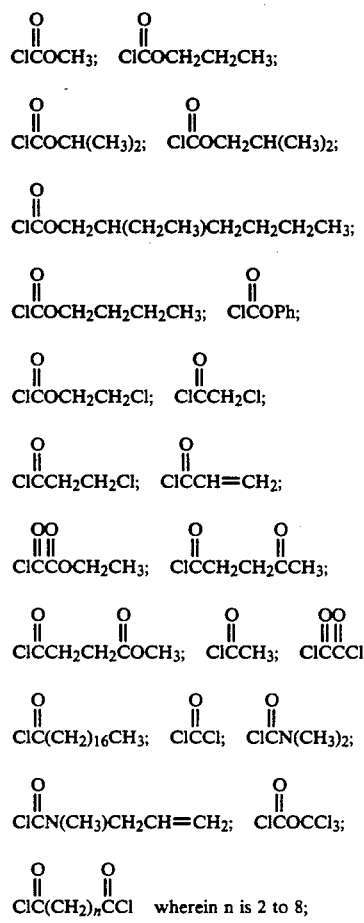

wherein n is 2 to 8;

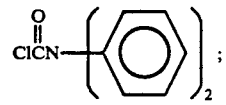

and

The most preferred acid halides are methyl chloroformate, n-butyl chloroformate, phenyl chloroformate, 2-chloroethyl chloroformate, ethyl chloroformate, propyl chloroformate, isopropyl chloroformate, isobutyl chloroformate, 2-ethylhexyl chloroformate, chloroacetyl chloride, 4-chlorobutyryl chloride, acryloyl chloride, methacryloyl chloride, oxalyl chloride, ethyloxalyl chloride, benzoyl chloride, para-nitrobenzoyl chloride, acetyl chloride, stearoyl chloride, and phosgene.

THE ACID AMIDE PRODUCTS

The acid amide products resulting from the reaction of haloaminotriazines and acid halides described above are represented, when M=1, by the formula:

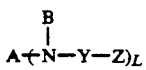

wherein A, B, Y, Z, and L are as defined previously above.

In cases where M is greater than 1 but L is equal to 1, the acid amide products of the invention may be represented by the formula:

wherein A, B, Y, Z, and M are as defined previously above.

In cases where both L and M are equal to 2, a linear amide oligomer or polymer may be formed.

Lastly, in cases where one of either L or M is at least 2, and the other one is greater than 2, a crosslinked polyamide network may be formed.

An example of the acid amide products of the invention resulting from the reaction of N,N',N''-trichloromelamine with methyl chloroformate is the triazine tris-carbamate represented by the formula:

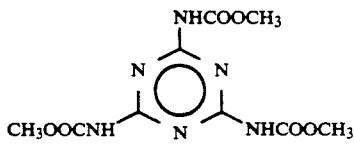

Another example resulting from the reaction of N,N',N''-trichloromelamine and 4-chlorobutyryl chloride is N,N'N''-tris(4-chlorobutyryl) melamine represented by the formula:

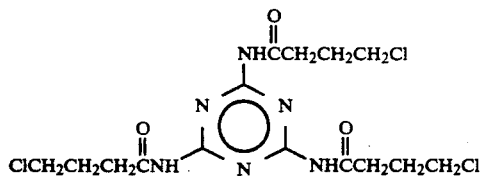

Another example of the acid amide products resulting from hexachloromelamine and methyl chloroformate is the triazine trichloro tris-carbamate represented by the formula:

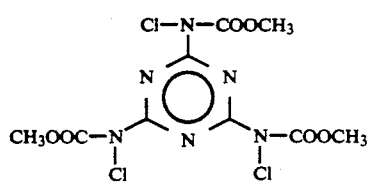

The trichloro tris-carbamate product may be readily reduced to the corresponding N—H compound using well known reducing agents such as alcohol/triethylamine, hydrogen halide, or sulfur compounds. The reduction product is the triazine tris-carbamate and is identical with a sample previously prepared by the more direct reaction of N,N',N''-trichloromelamine and methyl chloroformate described above. The amine-methanol reduction step is depicted below:

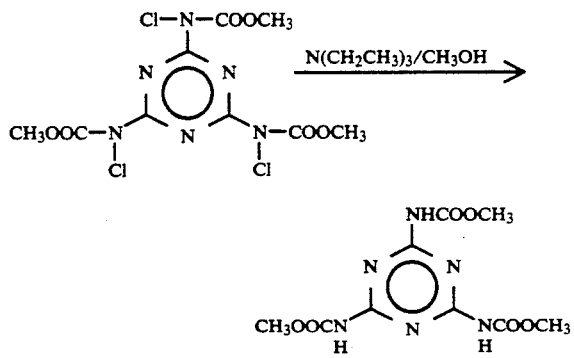

THE NOVEL PROCESS

The novel process of the invention comprises contacting a haloaminotriazine with an acid halide at a temperature and for a length of time sufficient to produce an acid amide as a product and halogen as a by-product.

The preferred reaction temperature is in the range of from about $-20°$ C. to about $120°$ C., although higher or lower temperature may be employed. The reaction is typically carried out at about $70°$ C., but any temperature at which no significant decomposition of starting materials occurs is generally suitable.

The preferred reaction time is in the range of from about 10 minutes to about 24 hours. The reaction is typically complete within a 2 to 8 hour period at about $70°$ C.

The process may be carried out as a continuous or batch process. It is typically carried out by simply admixing, in any order, the haloaminotriazine and the acid halide reactants. Alternatively, an excess of one of the reactants may be used as a liquid medium to carry out the amide forming reaction. The liquid medium, however, is typically a solvent for the haloaminotriazine and acid halide. The solvent is typically an aprotic solvent inert to chlorine or to the reactants. The reaction may also be carried out as a two phase reaction exemplified as a liquid/solid two phase reaction.

The preferred solvent in the process of the invention is a halogenated solvent. Most preferably, the halogenated solvent is selected from the group consisting of methylene chloride, chloroform, carbon tetrachloride, 1,1,1-trichloroethane, chlorobenzene, ortho-dichlorobenzene, 1,2-dichloroethane, and a mixture of the least two of any of the aforementioned solvents.

The reactants may generally be mixed in varying amounts, however at least one equivalent of acid halide per one equivalent of haloaminotriazine is generally required. The use of excess acid halide is preferred, particularly when the acid halide used is volatile, and therefore easily removable by distillation, or when the acid halide is used as a solvent in which the amide forming reaction of the invention is carried out.

The reactants may be admixed with or without a solvent conveniently at room temperature, or at below ambient temperature particularly when the reaction is exothermic. In endothermic reactions, after admixing the reactants at room temperature, the reaction mixture is typically heated to accelerate product formation.

The reaction is usually carried out in an atmosphere of an inert gas under moisture free conditions. This minimizes the decomposition of reactants by atmospheric moisture and also minimizes the formation of undesirable hydrogen halide which may form from the reaction of moisture with the reactants.

Under the conditions of the process of the invention, the halogen by-product produced during the reaction is substantially free of hydrogen halide.

A rate accelerating catalyst such as trialkyl and triaryl phosphines, quaternary ammonium halides, or a monomeric or a polymeric 4-dialkylaminopyridine derivative may be added to the reactants, however, the process is typically carried out without adding a catalyst.

Suitable dialkylaminopyridine catalysts include 4-dimethylaminopyridine, 4-pyrrolidinopyridine, 4-piperidinopyridine, and poly-2-vinyl-4-dimethylaminopyridine (polydimethylaminopyridine). Suitable quaternary ammonium halides include ALIQUAT® 336 tricapryl methyl ammonium chloride, available from Kodak Laboratory Chemicals, Rochester, N.Y.

When the acid amide reaction product is obtained as a solution, a process further comprising isolating the reaction product by removing the volatiles under reduced pressure may be used. The volatiles may be removed by distillation. Alternatively, or after removing the volatiles and redissolving the residue in a solvent, the amide maybe precipitated by adding a solvent in which the amide is substantially insoluble.

The product may be further purified by recrystallization, distillation, or chromatography.

PROCESS FOR PRODUCING ACID AMIDES FROM MELAMINE BY RECYCLING THE HALOGEN BY-PRODUCT

It is the discovery of this invention that melamine may be converted to an acid amide by two different processes, each involving recycling of the halogen by-product. No input of additional halogen is required except to make up for incidental halogen losses.

The conversion in the first novel process is via the trihalomelamine, and in the second novel process, the conversion is via the hexahalomelamine.

Both first and second processes are characterized by the following: the halogen by-product is recycled for use to convert additional melamine to hexahalomelamine. The two processes differ in that the first process comprises a step wherein a trihalomelamine is contacted with an acid halide, whereas the second process comprises a step wherein a hexahalomelamine is contacted with an acid halide.

The novel first and second processes comprising halogen recycle are described further below:

FROM TRIHALOMELAMINE

The first method is a process for producing an acid amide, more specifically, a triazine tris-acid amide from melamine via the trihalomelamine comprising the steps of:

(a) contacting said melamine with a halogen to produce hexahalomelamine;
(b) contacting melamine with hexahalomelamine to produce trihalomelamine; and
(c) contacting said trihalomelamine with an acid halide at a temperature and for a length of time sufficient to produce triazine tris-acid amide as a product and halogen as a by-product; and
(d) recycling the halogen by-product into step (a) to halogenate melamine to hexahalomelamine.

Steps (a) and (b) of this process is carried out by the procedures disclosed in U.S. Pat. Nos. 2,472,361; 2,184,888; 2,184,886; and 2,184,883; and in European Patent No. 239,121.

Step (c) is carried out under conditions described previously hereinabove in the section entitled "THE NOVEL PROCESS".

Recycling step (d) is carried out by removing the halogen by-product by means such as a stream of a carrier inert gas and collecting the halogen vapors by bubbling through an aqueous caustic solution to form a hypohalite solution to be used as the halogenating agent. The preferred halogens which are best suited for recycling are chlorine and bromine. Chlorine is the most preferred halogen.

Alternatively, the halogen may be collected in an organic solvent and used as such to halogenate additional melamine.

FROM HEXAHALOMELAMINE

The second method is a process for producing an acid amide, more specifically, a triazine tris-acid amide from melamine via the hexahalomelamine comprising the steps of:

(I) contacting said melamine with a halogen to produce hexahalomelamine and producing hydrogen halide as a by-product;
(II) contacting said hexahalomelamine with an acid halide at a temperature and for a length of time sufficient to produce triazine N,N',N"-trihalo tris-acid amide as an intermediate product and halogen as a by-product; and
(III) contacting the triazine N,N',N"-trihalo tris-acid amide intermediate of step (II) with hydrogen halide to produce triazine tris-acid amide as a final product and additional halogen as a by-product; and
(IV) recycling the halogen by-product of steps (II) and (III) into step (I) to halogenate melamine to hexahalomelamine.

Step (I) of this process is carried out by the procedures disclosed in U.S. Pat. Nos. 2,472,361; 2,184,888; 2,184,886; and 2,184,883.

Step (II) is carried out under conditions described previously hereinabove in the section entitled the "THE NOVEL PROCESS".

Step (III) is carried out by introducing hydrogen halide slowly, over a period of several minutes to several hours, into the reaction mixture at a temperature in the range of −20° to 120° C.

The preferred halogen halides are hydrogen chloride and hydrogen bromide. Gaseous hydrogen chloride is the most preferred hydrogen halide.

Recycling step (IV) is carried out by removing the halogen by-product from both steps (II) and (III) with a stream of a carrier inert gas and with collecting the halogen vapors by bubbling through an aqueous caustic solution to be used as the halogenating agent. The preferred halogens which are best suited for recycling are chlorine and bromine. Chlorine is the most preferred halogen.

Alternatively, the halogen may be collected in an organic solvent and used as such to halogenate additional melamine.

The process of the invention may be better understood by reference to FIG. 1 and FIG. 2 as follows:

TRIS-CARBAMATE FROM TRICHLOROMELAMINE (FIG. 1)

Thus, in FIG. 1 illustrating the process for producing triazine tris-methyl carbamate from melamine via trichloromelamine, melamine is introduced via line (1) and chlorine via line (2) into a reaction zone A (3) of the process and form hexachloromelamine.

Hexachloromelamine is then sent via line (4) and additional melamine via line (5) into reaction zone B (6) of the process to form trichloromelamine by a chlorine exchange reaction between melamine and hexachloromelamine.

Trichloromelamine is then sent via line (7) and methyl chloroformate via line (8) into a reaction zone C (9) of the process to form:

1. triazine tris-methyl carbamate as the product which is removed via line (10), and
2. chlorine gas as the by-product which is recycled via line (11) into zone A (3).

TRIS-CARBAMATE FROM HEXACHLOROMELAMINE (FIG. 2)

Figure 2:
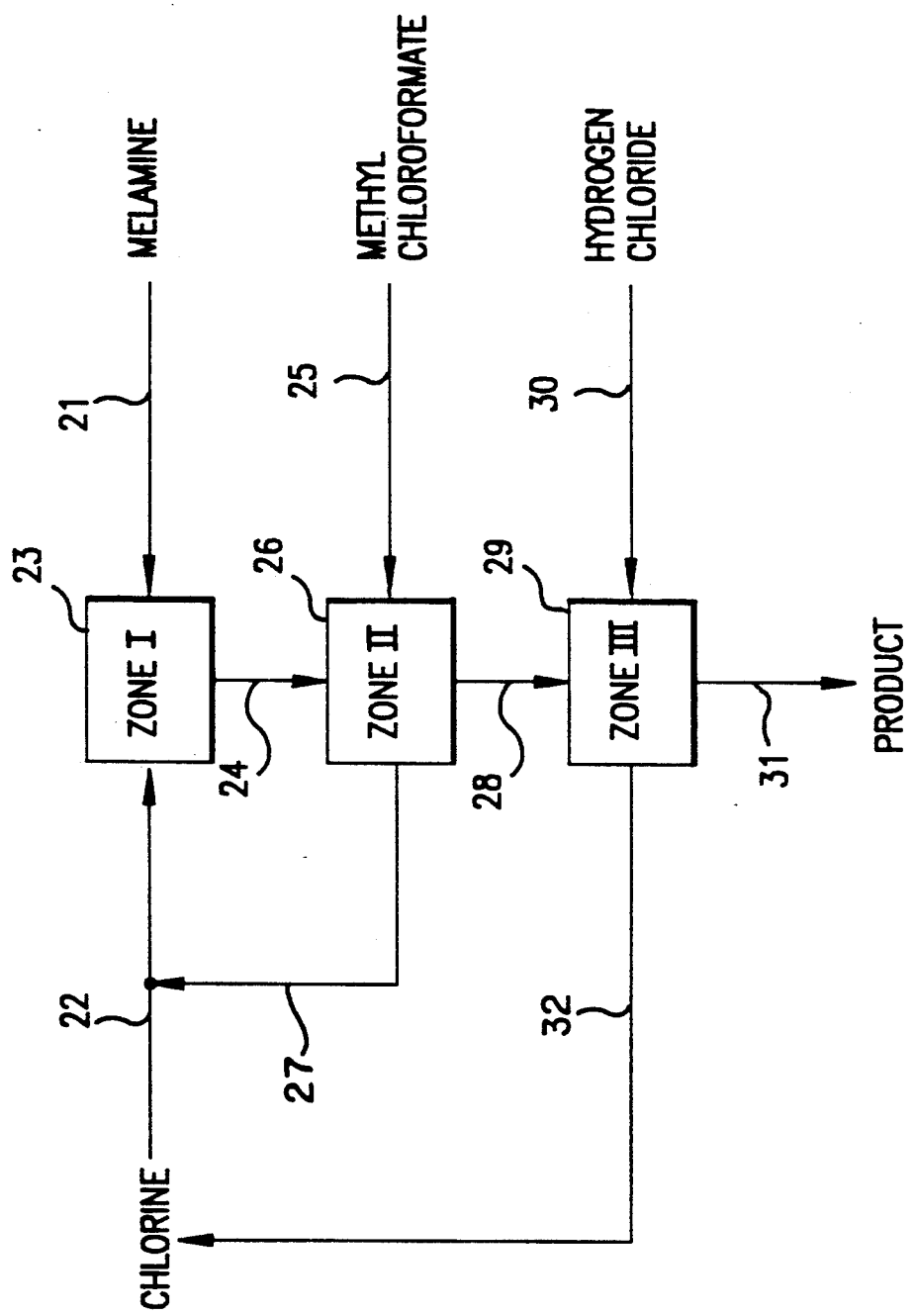
FIG. 2 schematically illustrate a process for producing triazine tris-methyl carbamate from melamine via hexachloromelamine.

In FIG. 2 illustrating the process for producing triazine tris-methyl carbamate from melamine via hexachloromelamine, melamine is introduced via line (21) and chlorine via line (22) into reaction zone I (23) of the process to form hexachloromelamine.

Hexachloromelamine is then sent via line (24) and methyl chloroformate via line (25) into reaction zone II (26) of the process to form:

1. N,N',N"-trichloro triazine tris-methyl carbamate as an intermediate product to be reacted further, and
2. chlorine gas as the by-product which is recycled via line (27), to line (22), into zone I (23).

The intermediate product N,N',N"-trichloro triazine tris methyl carbamate is then sent via line (28) and hydrogen chloride gas via line (3) into reaction zone III (29) of the process to form:

1. triazine tris-methyl carbamate as the final product which is removed via line (31), and
2. additional chlorine gas as the by-product which is recycled via line (32), to line (22), into zone I (23).

PROCESS FOR PREPARING ISOCYANATES AND ISOCYANATE ADDUCTS

The process of this invention may also be employed to prepare isocyanates by contacting a haloaminotriazine with an acid halide selected from the group consisting of oxalyl chloride, phosgene and phosgene analogs to form an acid amide intermediate and decomposing the intermediate to an isocyanate.

The acid amide intermediates are preferentially prepared in the same manner as discussed above for the acid amides of this invention. When the acid halide employed is oxalyl chloride or phosgene, the resulting acid amide intermediate is expected to be carbamoyl carbonyl chloride or carbamyl chloride, respectively. Exemplary phosgene analogs include, without limitation, diphosgene and triphosgene. Triphosgene (trichloromethyl carbonate) is understood by those skilled in the art to be a phosgene source. See, e.g., M. J. Coghlan and B. A. Caley, "Trichloromethyl Carbonate as a Practical Phosgene Source" Tetrahedron Letters, Vol. 30, No. 16, pp. 2033–2036 (1989).

The isocyanate is made by decomposing the intermediate. This decomposition can be accomplished by heating the intermediate or adding a base to act as either a catalyst or an acid scavenger. A typical base is triethylamine.

Preferentially, the intermediate is decomposed to isocyanate by heating. The preferred decomposition temperature for forming the isocyanate from the acid amide intermediate is in the range of from about 40° C. to about 140° C., although a higher or lower temperature may be employed if decomposition occurs. The reaction is typically carried out at about 100° C. to 110° C., but any temperature which will cause the acid amide intermediate to decompose to an isocyanate is sufficient.

The preferred reaction time for decomposing the acid amide intermediate to the isocyanate is in the range of about 1 hour to about 24 hours, although the time may be varied particularly depending on the temperature at which the reaction takes place.

It is not necessary to isolate the acid amide intermediate prior to its decomposition to isocyanate. However, if desired, the intermediate may be isolated from the reaction mixture prior to decomposition. Preferably, the acid amide intermediate is decomposed without isolating the intermediate from the reaction mixture, which typically also contains a halogenated solvent, such as ortho-dichlorobenzene.

The process of this invention may be further employed to prepare isocyanate adducts by reacting the isocyanates prepared by the above-described process with active hydrogen-containing compounds. The active-hydrogen containing compounds employed in this process include those known to one skilled in the art which have at least one active-hydrogen moiety selected from the group consisting of carboxyl, hydroxy, thiol, sulfonamide, amido, primary amine, secondary amine, salts thereof and mixtures thereof.

The active-hydrogen containing compounds employed in this invention include known blocking agents. For example, the active-hydrogen containing compound can comprise an aliphatic alcohol having one to twelve carbons, such as methyl, ethyl, chloroethyl, propyl, butyl, amyl, hexyl, 2-ethylhexyl, octyl, nonyl, 3, 3, 5-trimethylhexyl, decyl and lauryl alcohols and the like, cycloaliphatic alcohols such as cyclopentanol and cyclohexanol, aromatic alkyl such as phenyl carbinol, and phenols, such as phenol, o-, m-, and p-cresol, p-chlorophenol, beta naphtol and the like, as well as polyols such as ethylene glycol, propylene glycol, diethylene glycol, and the like.

The active-hydrogen containing compounds may also comprise other known blocking groups which deblock at relatively low temperatures, e.g. below about 125° C., such as an oxime of an aldehyde or ketone (e.g., methylethyl-ketoxime, acetone oxime and cyclohexanone oxime), lactam (e.g., caprolactam), hydroxamic acid ester, imidazole, pyrazole, N-hydroxyimide (e.g., N-hydroxyphthalimide), dimethylamine, or other blocking groups such as recited in U.S. Pat. No. 4,444,954 the pertinent portions of which are incorporated by reference herein.

Other active hydrogen-containing compounds, besides blocking agents, may also be employed in the process of this invention to obtain isocyanate adducts having various functional groups appended to the acid amide. For example, 4-amino-2,2,6,6,-tetramethyl piperidine can be reacted with an isocyanate to produce an isocyanate adduct having a urea linkage, the product of which may be a hindered amine light stabilizer. Additionally, an active hydrogen-containing compound containing two or more active-hydrogen moieties may be employed resulting in an isocyanate adduct having an unreacted active-hydrogen moiety.

Most preferably, the active hydrogen-containing compound used in the process of this invention includes aliphatic alcohols having 1 to 18 carbons, such as methanol, ethanol, isopropanol, propanol, isobutanol, butanol, tertiary butanol, pentanol, hexanol, heptanol, octanol, nonanol, decanol, lauryl alcohol, 2-ethyl hexanol, alkyl alcohol, glycidol and stearyl alcohol.

Since the reaction of the isocyanate with the active hydrogen-containing compound is generally an exothermic reaction, the reaction temperature is preferably in a range of from about $-20°$ C. to about $100°$ C. Most preferably the reaction mixture is cooled to about $0°$ C. prior to adding the active hydrogen containing compound to the isocyanate.

Typically, the reaction mixture is stirred and chilled for a time ranging from about 5 minutes to about two hours after adding the active hydrogen-containing compound to the isocyanate. Generally, this mixture is then brought to room temperature and stirred for a time ranging from about 10 minutes to about ten hours. The isocyanate adducts may be isolated in any desired manner, such as by distillation of the solvent, followed by distillation of the residue under vacuum and purification by recrystallization.

The process of preparing the isocyanates and isocyanate adducts of this invention are particularly preferred when the starting haloaminotriazine is a halomelamine or a haloguanamine. In particular the process may be employed to prepare triazine tris-isocyanate or a triazine tris carbamate, such as triazine tris butyl carbamate.

UTILITY

Products prepared by the processes of the invention have utility in diverse areas. In general, the utility of a particular product depends on its class.

A. TRIAZINE TRIS-CARBAMATES

In curable compositions, members of the triazine tris-carbamate class have utility as cross-linking agents for polyfunctional active hydrogen compounds, including hydroxyfunctional and aminofunctional materials, as disclosed in detail in U.S. Pat. No. 4,939,213 cited previously hereinabove. The curable compositions disclosed therein may be used in solvent-based, water-based, or powder coatings or they may be used as aqueous dispersions which are particularly suited to application by electrodeposition. They are thus useful in catalyzed or uncatalyzed, one component heat cured systems, for applications such as coatings, particularly powder coatings, coil coatings, and can coatings. They are also usable in non-coatings applications such as conventional moldings, reactive injection moldings, composites, adhesives, and binders.

The triazine tris-carbamates of the invention have utility as intermediates leading to other crosslinkers. For example, they may be pyrolized to give triazine triisocyanates which themselves are excellent crosslinking agents as disclosed in U.S. Pat. No. 4,939,213.

The triazine tris-carbamates of the invention have utility as intermediates leading to polymer additives. They may be further converted to ultraviolet (UV) light stabilizers by substitution of at least one alkoxy or aryloxy group in the triazine tris-carbamates prepared by the process of this invention. The product may be a hindered amine light stabilizer (HALS).

For example, reaction of triazine tris-phenylcarbamate with 4-amino-2,2,6,6-tetramethyl-piperidine at $25°$ C. to $160°$ C. temperature range produces, in good yield, a tris-urea derivative of melamine having the chemical name of tris-(2,2,6,6-tetramethyl-piperid-4-yl-aminocarbonyl) melamine represented by the formula:

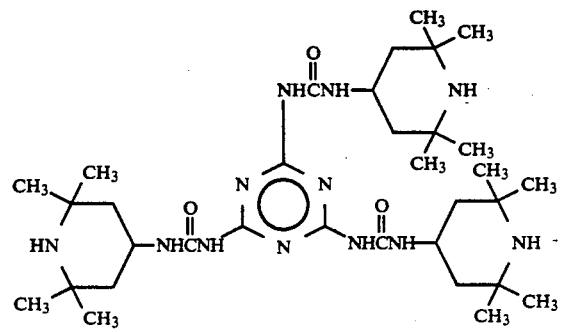

B. TRIACYL MELAMINES

An example of triacyl melamine class is the N,N',N"-tristearylmelamine which has utility in polishing waxes and in water repellant fabric finishes as disclosed in U.S. Pat. No. 2,507,700.

C. TRIS-(OMEGAHALOACYL) MELAMINES

Another class of compounds which may be prepared by the process of the invention is the tris-(omegahaloacyl) and related melamine classes represented by the formula:

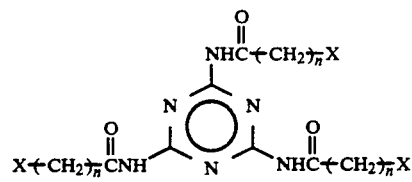

wherein n is an integer from 1 to 5; and x is a leaving group selected from the group consisting of chloride, bromide, iodide, flouride, alkylsulfonate, arylsulfonate, and mixtures thereof.

The preferred compounds are those wherein x is chloride and n is 3 or 4.

D. LACTAM SUBSTITUTED TRIAZINE CROSSLINKERS

The tris-(omegahaloacyl) melamines of the invention are intermediates leading to the preparation of lactam-substituted triazine crosslinkers reprensented by formula:

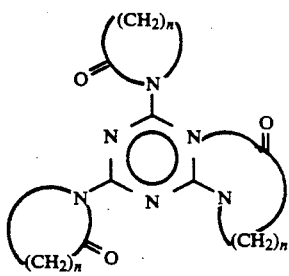

wherein n is an integer from 1 to 5.
The preferred lactam-substituted triazine crosslinkers of the invention are those wherein n is 3 or 4.

PREPARATION OF THE LACTAM CROSSLINKERS

The tris-lactam substituted triazine crosslinkers of the invention described in the immediately preceding paragraphs above are easily prepared from the corresponding tris-(omegahaloacyl)-melamines via an intramolecular cyclization reaction upon the action of a strong base, typically in a non-protic solvent having a high dielectric constant for dissolving the various ionic intermediates at room temperature.

The intramolecular cyclization may be carried out at about 0° C. to about 120° C. in a period of time in the range of from 10 minutes to 24 hours.

However, it is usually sufficient to carry out the intramolecular cyclization reaction at room temperature for a period of one to 6 hours only.

The product is isolated by adding a water-ice mixture to the reaction mixture to precipitate the lactam crosslinkers of the invention. Alternatively, the product may be extracted.

An example of tris-(omegahaloacyl)-melamine class is N,N',N''-tris-(4-chlorobutyryl)-melamine represented by the formula:

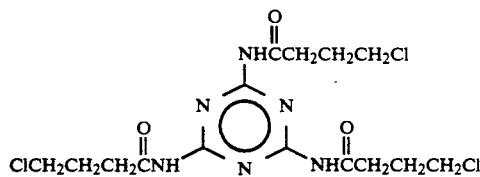

which has utility of being an intermediate leading to the N-substituted pyrrolidine crosslinking agent 2,4,6-tris-(-pyrrolidin-2-on-1-yl)-1,3,5-triazine, the utility of which as thermosetting resin material and hardening agents are disclosed in JP 58 146582. The tris-(N-pyrrolidonly)-triazine is represented by the formula:

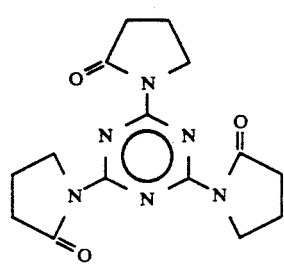

and may be easily prepared by a based-catalyzed intramolecular cyclization reaction of each of the 4-chlorobutyrylamino groups of the N,N'N''-tris-(4-chlorobutyryl) melamine precursor.

E. N-HALO ACID AMIDES

Another class of compounds which may be prepared by the process of the invention is N-halo acid amide intermediate products of the invention potentially useful as herbicides and pesticides as suggested by U.S. Pat. Nos. 3,920,832; 4,732,899; and 4,824,845.

A typical N-halo acid amide product of the invention is a composition of matter represented by formula:

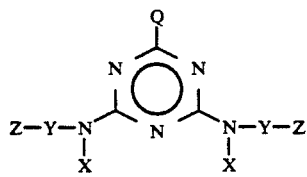

wherein Q is —N—Y—Z; or
           |
           X

Q is selected from the group consisting of alkyl of 1 to 20 carbon atoms, cyclic or branched alkyl of 3 to 20 carbon atoms, alkenyl of 2 to 20 carbon atoms, aryl of 6 to 20 carbon atoms, aralkyl of 7 to 20 carbon atoms, alkoxy of 1 to 20 carbon atoms, aryloxy of 6 to 20 carbon atoms, alkylthio of 1 to 20 carbon atoms, arylthio of 6 to 20 carbon atoms, alkylamino of 1 to 20 carbon atoms, dialkylamino of 2 to 40 carbon atoms, morpholino, piperidino, pyrrolidino, aminotriazino, alkylaminotriazino, aminoalkylaminotriazino, hydrogen, chloro, bromo, iodo, fluoro, perfluoralkyl, perfluoroaryl, perfluoroaralkyl groups; and wherein X in each —N—Y—Z group is hydrogen or
                    |
                    X a halogen with the proviso that at least one halogen independently selected from the group consisting of chloride, bromide, iodide, and fluoride; and Y in each —N—Y—Z group is
           |
           X the same or different and each is independently selected from the group consisting of the following functionalities represented by the formula:

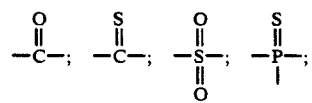

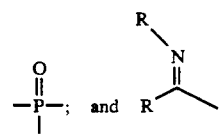

wherein each R is independently an alkyl, aryl, or an alkoxy group; and

Z is an M-functional anchor selected from the group consisting of hydrogen, chloro, bromo, iodo, fluoro, vinyl, alkyl of 1 to 20 carbon atoms, haloalkyl of 1 to 20 carbon atoms, alkylene of 1 to 20 carbon atoms, arylene of 6 to 20 carbon atoms, aryl of 6 to 20 carbon atoms, haloaryl of 6 to 20 carbon atoms, haloaryl of 6 to 20 carbon atoms, aralkyl of 7 to 20 carbon atoms, haloaralkyl of 7 to 20 atoms, acyl of 2 to 20 carbon atoms, haloacyl of 2 to 20 carbon atoms, halocarbonyl, alkoxycarbonyl of 2 to 20 carbon atoms, alkylthiocarbonyl of 2 to 20 carbon atoms, haloalkoxy of 2 to 20 carbon atoms, aminocarbonyl, alkylaminocarbonyl of 2 to 20 carbon atoms, dialkylaminocarbonyl of 3 to 20 carbon atoms, alkenylaminocarbonyl of 4 to 20 carbon atoms, dialkenylaminocarbonyl of 7 to 40 carbon atoms, alkylalkenylaminocarbonyl of 5 to 20 carbon atoms, triazino, pyrimidino, pyridino, imidazole, tetrazole, perfluoroalkyl of 1 to 20 carbon atoms, perfluoroaryl of 6 to 20 carbon atoms, perfluoro aralkyl of 7 to 20 carbon atoms, haloalkyl of 1 to 20 carbon atoms, alkoxycarbonylalkyl of 3 to 20 carbon atoms, cyanoalkyl of 2 to 20 carbon atoms, formylalkyl of 2 to 20 carbon atoms, ketoalkyl of 3 to 20 carbon atoms, trialkoxysilylalkyl of 4 to 20 carbon atoms, dialkylaminoalkyl of 3 to 20 carbon atoms, alkoxyalkyl of 2 to 20 carbon atoms, alkoxy of 1 to 20 carbon atoms, aryloxy of 6 to 20 carbon atoms, alkenyloxy of 3 to 20 carbon atoms, alkylenedioxy of 2 to 20 carbon atoms, arylenedioxy of 6 to 20 carbon atoms, N,N-dialkylamino of 2 to 40 carbon atoms, N,N-dialkenylamino of 6 to 40 carbon atoms, N,N-diarylamino of 12 to 40 carbon atoms, N,N-alkylalkenylamino of 4 to 20 carbon atoms, N,N-alkylarylamino of 7 to 20 carbon atoms, N,N-alkenylarylamino of 9 to 20 carbon atoms, aziridino, azetidino, pyrrolidino, piperidino, morpholino, alkylmercapto of 1 to 20 carbon atoms, alkenylmercapto of 3 to 20 carbon atoms, and arylmercapto of 6 to 20 carbon atoms.

The products prepared by the process of the invention are obtained by contacting haloaminotriazine and acid chloride reactants under the process conditions described above. They may comprise carboxylic acid amides, carbamates, sulfonamides, phosphoramides, ureas, thioureas, thiophosphoramides, amidines, amidate esters, and mixtures thereof. In addition, isocyanate products may be obtained by decomposing acid amide intermediates, such as carbamoyl chlorides, and carbamoyl carbonyl chlorides produced by contacting a haloaminotriazine with specific acid chlorides such as phosgene or oxalyl chloride. Also, isocyanate adducts, such as carbamates and ureas, are obtained by contacting active hydrogen-containing compounds with the isocyanates produced in accordance with this invention.

The following examples illustrate the various embodiments of the invention.

EXAMPLE 1

Triazine Trismethylcarbamate From Hexachloromelamine

A mixture of 3.33 g of hexachloromelamine, 23.6 g methyl chloroformate and 200 mg polydimethylaminopyridine was heated at 70° C. for 6 hours under argon. The excess methyl chloroformate was removed under reduced pressure. The residue was cooled and dissolved in a 50 ml methanol and 25 ml $CH_2Cl_2$ mixture. It was then treated with 5 ml triethylamine dropwise while cooling. The mixture was concentrated and the residue treated with methanol. Triazine trismethlycarbamate crystallized out which was filtered and characterized by $^1H$ NMR, $^{13}C$ NMR, IR and Fast Atom Bombardment (FAB) mass spectroscopy (2.4 g; 80%);

m.p. greater than 300° C.; decomposition started at about 220° C. and peaked at about 250° C.;

$^1H$ NMR (CDCl3, delta): 3.8 (s, 9H, 3X OC$\underline{H}_3$) 8.8 (s, 3X N$\underline{H}$);

$^{13}C$ NMR (DMSO-d6, delta): 52.3, 151.9, 164.9
IR (CHCl3) 1760 cm$^{-1}$ (C=O);
MASS (FAB, M+H+): 301.

EXAMPLE 2

Triazine Trismethylcarbamate From Trichloromelamine (Solventless Process)

A mixture of 2.3 g trichloromelamine, 20 ml methylchloroformate and 200 mg poly-dimethylaminopyridine was heated under argon at 75° C. for 3 hours. The excess methyl chloroformate was removed under reduced pressure. The residue was dissolved in a mixture of 100 ml methanol and 50 ml $CH_2Cl_2$. To it was added 1 ml $Et_3N$ dropwise. It was filtered and solvent removed from the filtrate under reduced pressure. The residue on treatment with 20 ml methanol gave a crystalline produce characterized to be triazine trismethylcarbamate (2.27 g; 76%), identical with the product by Example 1.

EXAMPLE 3

Triazine Trisbutylcarbamate From Trichloromelamine (Dichlorobenzene Solvent)

A mixture of 11.5 g trichloromelamine, 57.2 ml n-butylchloroformate and 50 ml o-dichlorobenzene was heated under Argon with stirring at 58°-62° C. for 5 hours. It was allowed to cool to room temp. and diluted with 30 ml o-dichlorobenzene. 40 ml liquid was then collected by heating the reaction mixture at 55° C. under reduced pressure. The residue was cooled and diluted with 300 ml hexane. The precipitated material was then filtered and washed with 200 ml hexane. The residue was purified by silica gel column chromatography using $CH_2Cl_2$/MeOH (97:3) as the eluant. Triazine trisbutylcarbamate so obtained was identified by $^1H$ NMR, $^{13}C$ NMR and mass spectroscopy (17.2 g; 81% yield);

m.p. 149.5°-51° C.;

$^1H$ NMR (CDCl3, delta): 0.9(t, 9H, 3X C$\underline{H}_3$CH2CH2O—), 1.3(m, 6H, 3X $\overline{C}$H3C$\underline{H}_2$CH2CH2O—), 1.6 (m, 6H, 3 X CH3$\overline{C}$H2C$\underline{H}_2$CH2—), 4.1(t, 6H, 3X CH3CH2C$\underline{H}_2$CH2O—), 8.7 (s, 3H, 3XNH);

$^{13}C$ NMR ($\overline{C}$DCl3, delta): 8, 20, 66, 150, 164; MASS (FAB, M+H+): 427.

EXAMPLE 4

Triazine Trisphenylcarbamate From Trichloromelamine (Carbon Tetrachloride Solvent)

A mixture of 2.3 g. trichloromelamine, 10.0 ml phenyl chloroformate and 40 ml $CCl_4$ was heated under argon at 50° C. for 3 hours. It was cooled to room temperature and filtered. The residue was dissolved in a mixture of $CH_2Cl_2$/MeOH and solvent evaporated under reduced pressure. The residue was treated with anhydrous methanol and the precipitate formed was filtered and dried (4.2 g; 86% yield). The product thus obtained was characterized to be triazine trisphenylcarbamate by $^1$H NMR, $^{13}$C NMR, IR and mass spectroscopy;

Deblocking (decomposition) started at about 100° C. and peaked at about 160° C.;

$^1$H NMR (DMSO-d$_6$, delta): 7.2–7.5 (m, 15H, 3X ArH$_5$), 11.2 (s, 3H, 3XN$\underline{H}$);

$^{13}$C NMR (DMSO-d$_6$, delta): 122, 126, 129, 149, 151, 165;

MASS (FAB, M+H+): 487.

EXAMPLE 5

N,N',N''-Tris(4-Chlorobutyryl) Melamine

A mixture of 2.3 g trichloromelamine, 20 ml carbon tetrachloride, 8.46 g 4-chlorobutyryl chloride and 30 mg N,N-dimethylaminopyridine was placed in a 100 ml flask fitted with a magnetic stirring bar, a reflux condenser and argon inlet. The reaction mixture was slowly heated in an oil bath to 60° C. and was stirred at 60° C. for 5 hours. It was then allowed to cool down to room temperature and diluted with 50 ml hexanes. The contents were stirred at room temperature for 30 minutes and then filtered. The residue was washed with hexane and dried under reduced pressure. It was characterized to be N,N',N''-tris(4-chlorobutyryl) melamine on the basis of NMR and mass spectroscopy (4.2 g; 95% yield);

$^1$H NMR (DMSO-d$_6$, delta): 2.0 (m, 6H, 3X C$\underline{H_2}$CH$_2$CH$_2$Cl), 2.8 (t, 6H, 3X NHCOC$\underline{H_2}$CH$_2$CH$_2$Cl), 3.6 (t, 6H, 3X CH$_2$C$\underline{H_2}$Cl), 11.8 (broad s, 3H, 3X N$\underline{H}$CO);

$^{13}$C NMR (DMSO-d$_6$, delta): 27, 34, 44, 161, 174;

MAS (FAB, M+H+): 439.

EXAMPLE 6

N,N',N'',-Trischloroacetyl Melamine 460 mg trichloromelamine was placed in a 3-neck 100 ml flask fitted with a reflux condenser, argon inlet, a magnetic stirring bar, and a rubber septum inlet. To the flask was added 10 ml carbon tetrachloride followed by 1.4 ml chloroacetylchloride with a syringe under stirring. The reaction mixture was heated up to 60° C. in an oil bath for 4.5 hours. It was then allowed to cool to room temperature and the excess reagent and carbon tetrachloride were removed under reduced pressure. The residue was diluted with hexane and the precipitated material filtered off, washed with hexane and dried under reduced pressure to give a product (689 mg; 97% yield) which was characterized to be N,N',N''-trischloroacetyl melamine based on $^1$H NMR, $^{13}$C NMR and mass spectroscopic data;

$^1$H NMR (DMSO-d$_6$, delta): 4.8 (s, 6H, 3X C$\underline{H_2}$Cl), 11.1 (s, 3H, 3X N$\underline{H}$CO);

$^{13}$C NMR (DMSO-d$_6$, delta): 45.8, 163.8, 167.1; MASS (FAB, M+H+): 355.

EXAMPLE 7

Triazine Trisethyl Carbamate

The procedure of Example 2 was repeated at 80° C. using ethyl chloroformate (20.0 ml) in the place of methyl chloroformate. The product was triazine trisethyl carbamate (2.2 g, 76% yield). m.p. greater than 300° C.; decomposition started at about 200° C. and peaked at about 260° C.

EXAMPLE 8

Triazine Trispropyl Carbamate

The procedure of Example 4 was essentially repeated using propyl chloroformate (10.0 ml) in the place of phenyl chloroformate. The product was triazine trispropyl carbamate. 2.3 g of trichloromelamine was placed in a 250 ml flask equipped with a magnetic stirring bar, a reflux condenser and an argon inlet. To it was added 50 ml CCl$_4$ followed by 10.0 ml propyl chloroformate. The reaction mixture was gradually heated in an oil bath to 75° C. and kept at 75° C. for 6 hours. Removal of the excess propyl chloroformate followed by usual workup gave a product which was characterized to be triazine tris-propyl carbamate by $^1$H NMR, $^{13}$C NMR, IR and mass spectroscopy; m.p. 178° to 182° C.

EXAMPLE 9

Triazine Tris-(2-chloroethylcarbamate)

The procedure of Example 4 was repeated using 2-chloroethyl chloroformate (3.5 ml) in the place of phenyl chloroformate. The product was triazine tris-(2-chloroethylcarbamate). The procedure was as follows:

To a stirring suspension of 1.15 g trichloromelamine in 30 ml CCl$_4$, in a 100 ml flask fitted with a reflux condenser, a magnetic stirring bar and argon inlet was added 3.5 ml (4.8 g) of 2-chloroethyl chloroformate. The reaction mixture was stirred at room temperature for 0.5 hours and then slowly heated in an oil bath to 75° C. The heating was continued for 6 hours and the reaction was then allowed to cool to room temperature. Excess 2-chloroethyl chloroformate and CCl$_4$ were removed under reduced pressure and the residue purified by column chromatography (silica gel) using CH$_2$Cl$_2$ and MeOH mixture (95:5) as the eluant to give triazine tris(2-chloroethyl) carbamate as characterized by $^1$H NMR, $^{13}$C NMR, mass and IR spectroscopy; m.p. 130° C. (decomp.)

EXAMPLE 10

Triazine Tris-(2-ethylhexylcarbamate)

The procedure of Example 4 was repeated using 2-ethylhexyl chloroformate (86.7 g) in the place of phenyl chloroformate. The product was triazine tris-(2-ethylhexylcarbamate). The procedure was as follows: A mixture of 11.5 g trichloromelamine, 150 ml o-dichlorobenzene and 86.7 g 2-ethylhexyl chloroformate was heated in a flask equipped with a magnetic stirring bar, an Argon inlet and a reflux condenser. The temperature of the oil bath was gradually increased to 67° C. After 6 hours at 67° C., the heating was discontinued and the reaction mixture concentrated under reduced pressure. Usual work-up of the reaction mixture gave a product which was characterized to be triazine tris-(2-ethylhexylcarbamate) on the basis of spectroscopic data.

EXAMPLE 11

Triazine Tris-(iso-butylcarbamate)

The procedure of Example 3 was slightly modified and isobutyl chloroformate (16.4 ml) was used in the place of n-butyl chloroformate. The product was triazine tris-(iso-butylcarbamate). The slightly modified procedure was as follows:

To a flask equipped with a magnetic stirring bar, a reflux condenser and an Argon inlet, 4.6 gm of trichloromelamine was added followed by 40 ml o-dichlorobenzene and 16.4 gm isobutyl chloroformate.

The reaction mixture was heated in an oil bath at 65°-70° for 6 hours. It was then allowed to cool and excess isobutyl chloroformate and o-dichlorobenzene were removed under reduced pressure. The residue was treated with 100 ml hexanes and the precipitated material filtered and washed with 50 ml hexane and dried. The product was characterized to be triazine tris-isobutyl carbamate by $^1$H NMR, $^{13}$C NMR, IR, and mass spectroscopy. It decomposed starting at about 230° C. and peaked at about 245° C.

EXAMPLE 12

Triazine Mixed Alkyl Carbamates

The procedure of Example 3 was essentially repeated using a mixture of haloformates consisting of 2-ethylhexyl chloroformate (4 ml) and methyl chloroformate (6.2 ml) in the place of n-butyl chloroformate. The product was a triazine tris-(mixed alkyl carbamate) wherein the mixed alkyl group consisted or 2-ethylhexyl and methyl groups in ratio in the range of from about 1:1.8 to about 1:0.77. The detailed experimental procedure was as follows:

A mixture of 4.6 g trichloromelamine, 4 ml 2-ethylhexyl chloroformate and 30 ml o-dichlorobenzene was heated under Argon with stirring at 60° C. for 4 hrs. It was allowed to cool at room temperature. Then 6.2 ml of methyl chloroformate was added. The reaction mixture was then heated under Argon with stirring to 65° C. for 2 hours. It was allowed to cool to room temperature and diluted with 15 ml of dichlorobenzene; 10.5 ml liquid was then collected by heating the reaction mixture to 40° C. under reduced pressure. The residue was cooled and diluted with 200 ml hexanes. The precipitated material was filtered and washed with 300 ml hexanes. Five gram of the solid was stirred with 250 ml methylene chloride and 2.6 g of insolubles were filtered off and identified to be the N-(2-ethylhexoxy-carbonylamino) -N', N"-di(methoxycarbonylamino) triazine with an ethylhexyl/methyl ratio of 1:1.8 by $^1$H NMR (52% yield). The methylene chloride solution was washed 2 times with 5% sodium bisulfite and 2 times with deionized water, dried over magnesium sulfate and stripped of solvent to give 1.86 gram of N-(ethylhexoxycarbonylamino)-N'-(methoxycarbonylamino) triazine with a ethylhexyl/methyl ratio of 1.3:1 (or 1:0.77) as identified by $^1$H NMR (37% yield).

EXAMPLE 13

N,N',N"-Tris-(3-chloropropionyl) Melamine

To a stirring suspension of 2.3 g trichloromelamine in 40 ml CCl$_4$ was added 7.62 g 3-chloropropionyl chloride under Argon. The reaction mixture was heated in an oil bath at 65°-70° C. for 6 hours. The reaction mixture was cooled and then diluted with 50 ml hexane. The precipitates were filtered, washed with hexane and dried under reduced pressure (3.9 g; 98% yield). The product thus obtained was characterized to be N'N',N"-tris (3-chloropropionyl) melamine by $^1$H NMR, $^{13}$C NMR, IR, and mass spectroscopy.

EXAMPLE 14

N'N',N"-Triacetyl Melamine

The procedure of Example 6 was repeated at room temperature for 20 hrs, using acetyl chloride (15 ml) in the place of chloroacetyl chloride. The product was triacetyl melamine.

EXAMPLE 15

N'N',N"-Trihexanoyl Melamine

The procedure of Example 6 was essentially repeated using hexanoyl chloride (8.07 g) in the place of chloroacetyl chloride. The product was trihexanoyl melamine. The experimental procedure as follows:

A mixture of 2.3 g trichloromelamine, 8.07 g hexanoyl chloride, and 25 ml carbon tetrachloride was heated with stirring under Argon for 6 hours at 70°-78° C. The reaction mixture was allowed to cool to room temperature and the product was precipitated by adding 100 ml hexane. The precipitated material was filtered, washed with 50 ml hexane and dried. Spectroscopic data were consistent with N'N',N"-trihexanoyl melamine structure.

EXAMPLE 16

N'N',N"-Tributyryl melamine

The procedure of Example 6 was essentially repeated using butyryl chloride (6.4 g) in the place of chloroacetyl chloride. The product was tri-butyryl melamine. The procedure was as follows:

2.3 g of trichloromelamine was treated with 6.4 g butyryl chloride in 40 ml CCl$_4$ at 65° C. for nearly 6 hours. The reaction mixture was cooled and diluted with 100 ml hexane. The precipitated material was filtered, washed with hexane and dried. Mass spectroscopic analysis indicated that the product was N'N',N"-tributyryl melamine.

EXAMPLE 17

N'N',N"-Tribenzoyl Melamine

The procedure of Example 6 was essentially repeated using benzoyl chloride (6.7 ml) in the place of chloroacetyl chloride. The product was tribenzoyl melamine. The procedure was as follows:

To a stirring suspension of 2.3 g of trichloromelamine in 40 ml CCl$_4$ in a flask equipped with a magnetic stirring bar, an Argon inlet and a reflux condenser was added 6.7 ml benzoyl chloride. The reaction mixture was heated in an oil bath at 68°-70° C. for 7 hours. The reaction mixture was then allowed to cool and then diluted with 30 ml hexane. The precipitated material was filtered off and the residue washed with 150 ml hexane and then dried under reduced pressure. (4.3 g; 98% yield). The product was characterized to be N'N',N"-tribenzoyl melamine by $^1$H NMR, $^{13}$C NMR, IR and mass spectorscopy.

EXAMPLE 18

N'N',N"-Tri-paranitrobenzoyl Melamine

The procedure of Example 6 was essentially repeated using para-nitrobenzoyl chloride (5.55 g) in the place of chloroacetyl chloride. The product was tri-paranitrobenzoyl melamine. The procedure was a follows:

To a stirring suspension of trichloromelamine (1.15 g) in CCl$_4$ (20 ml) was added a solution of 5.55 g of p-nitrobenzouyl chloride in 30 ml CCl$_4$. The reaction mixture was heated in an oil bath under an atmosphere of Argon at 70° C. for 6 hours, was allowed to cool and then was diluted with 25 ml CCl$_4$. The precipitates were filtered, washed with 100 ml CCl$_4$ and dried under reduced pressure. The product was characterized to be N'N',N"-tri-paranitrobenzoyl melamine by $^1$H NMR, $^{13}$C NMR spectroscopy.

EXAMPLE 19

Tris-(2,2,6,6-tetramethylpiperidin-4-yl-aminocarbonyl)-melamine

A mixture of the triaizine tris-phenylcarbamate (4.86 g) product of Example 4 and 4-amino-2,2,6,6-tetramethylpiperidine (15.4 ml) in toluene solvent (80 ml) was heated at 115° C. for 8 hours. After cooling, addition of hexane (100 ml), a tris-urea derivative characterized to be tris-(2,2,6,6-tetramethylpiperidin-4-yl-aminocarbonyl) melamine was obtained (5.95 g, 89% yield). It decomposed starting at about 220° C. and peaked at about 270°.

EXAMPLE 20

Preparation of 2,4,6-Tris(pyrrolidin-2-on-1-yl)-1,3,5-triazine from N,N'N"-Tris(4-chlorobutyryl)melamine Sodium hydride (200 mg, 60% in mineral oil) was placed in a 3-neck flask fitted with an Argon inlet, a stopper, a rubber septum and a magnetic stirring bar. To it was added 5 ml n-hexane and the mixture allowed to stir for several minutes. Stirring was stopped and with the help of a syringe, n-hexane was removed. To the washed NaH thus obtained was added 5 ml dimethylformamide (DMF). The flask was cooled to 0° C. in an ice-bath and 440 mg of N,N',N"-tris(4-chlorobutyryl)-melamine, the product of Example 5, dissolved in 5 ml DMF was added with stirring to the flask containing NaH. The reaction mixture was stirred at 0° C. for 5 hours. The cooling bath was then removed and the reaction mixture allowed to warm to room temperature. The reaction mixture was then slowly added to 100 ml ice-cold water. The reaction mixture was extracted with $CH_2Cl_2$ (3×30 ml) and the combined organic extract washed with water (20 ml) and dried over $MgSO_4$ was filtered and the filtrate concentrated under reduced pressure. The solvent was then removed and residue was dried under reduced pressure. The product was essentially a pure compound (270 mg, 82% yield) and was characterized to be 2,4,6-tris-(pyrrolidin-2-on-1-yl)-1,3,5-triazine by NMR and mass spectroscopy:

$^1$H NMR, (CDCl$_3$, delta): 2.0 (m, 6H, 3XCH$_2$CH$_2$—CH$_2$CO), 2.6 (t, 6H, 3X CH$_2$CH$_2$CO), 4.0 (t, 6H, 3X NCH$_2$CH$_2$); MASS (FAB, M+H+): 331.

EXAMPLE 21

A mixture of 1.15 g trichloromelamine, 30 ml CCl$_4$, 4.2 g benzoyl chloride and 50 mg ALIQUAT® 336 (tricaprylylmethylammonium chloride) in 0.5 ml CCl$_4$ was stirred at room temperature. Formation of chlorine indicated by the formation of yellow color was noticed within 20 minutes. Thin layer chromatographic analysis of the reaction mixture after 30 minutes indicated the formation of N,N',N"-tribenzoyl melamine.

In a second experiment, 1.15 g trichloromelamine was stirred in 30 ml CCl$_4$ with 4.2 g benzoyl chloride at room temperature, with no catalyst added. In this case no color was observed in 20 minutes. Furthermore, thin layer chromatographic analysis after 30 minutes and even after 4 hours indicated the absence of products corresponding to N,N',N"-tribenzoyl melamine.

It is concluded from these comparative experiments that the reaction of the invention is catalyzed by quaternary amine halides.

EXAMPLE 22

The procedure of Example 4 was essentially repeated using hexabromomelamine (5.2 g), prepared by the procedure described in U.S. Pat. No. 2,472,361.

The experimental details were as follows:

PART A: Preparation of Hexabromomelamine

In accordance to the procedure outlined by W. C. Arsem in U.S. Pat. No. 2,472,361:

4.1 grams of melamine was suspended in 100 grams of deionized water and 24.1 grams of glacial acetic acid was added. The mixture was cooled to about 5° C. and to it was added with stirring an aqueous solution containing 25 grams of sodium hypobromite in approximately 5 percent concentration over a period of 2 hours. Additional acetic acid was added during the course of the reaction to keep the pH below 7. Thirty minutes after completion of the NaOBr addition, the solid product was filtered off, washed with 700 ml of water, and dried under reduced pressure at room temperature. The product was a dark yellow powder (14.85 g; 88% yield) which was characterized by $^{13}$C NMR and IR. Titration for active bromine content gave a value of 8.97 mmol bromine per gram of product, which is 89.6% of the theoretical value.

PART B: Preparation of N,N',N"-Tribromo-2,4,6-Trismethoxycarbonylaminotriazine from Hexabromomelamine in Carbon Tetrachloride A mixture of 5.2 grams of hexabromomelamine, 9.45 grams of methyl chloroformate, and 50 ml of carbon tetrachloride was heated with stirring at 55°–75° C. for five hours under a nitrogen atmosphere. The evolution of BrCl vapor was observed during the course of the reaction. After cooling, the solid product was filtered off, washed with 200 ml of CCl$_4$, and dried under reduced pressure at room temperature.

The product was a yellow powder (2.30 g; 43% yield) which was analyzed by $^1$H NMR, $^{13}$C NMR, and IR. Titration for active bromine content gave a value of 5.85 mmol bromine per gram of product, which corresponds to 104.6% of the theoretical value. From the spectroscopic analysis and from the results of the titration, it was concluded the the product was N,N',N"-tribromo-N,N',N"-tris(methoxycarbonylamino-1,3,5-triazine).

EXAMPLE 23

PART A: N,N,N'-Trichlorobenzoguanamine from Benzoguanamine

A mixture of 18.72 g benzoguanamine, 24.25 ml glacial acetic acid, and 350 ml deionized water was cooled at 9° C. in an ice bath under Argon. To this was added with stirring 641 ml of 5% aqueous sodium hypochlorite over a period of 70 minutes at 9° C. The mixture was stirred for half an hour, filtered, and the residue washed with 700 ml deionized water. The solids were dried at room temperature under reduced pressure to give N,N,N'-trichlorobenzoguanamine. The product was identified by $^1$H NMR and IR spectroscopy and by chlorine titration to be the N,N,N'-trichlorobenzoguanamine (93% of the theoretical value of active chlorine); (27.93 g, 91.7% yield).

PART B: Preparation of 2,4-Di(butoxycarbonylamino)-6-phenyl-1,3,5-triazine from Trichloro Benzoguanamine.

A mixture of 2.5 grams of N,N,N'-trichloro-benzoguanamine, 5.5 ml butyl chloroformate, and 20 ml o-dichlorobenzene was heated under Argon with stirring at 70° C. for 8½ hours. It was cooled to room temperature and 125 ml of hexane was added. The mixture was filtered and the solids dried under reduced pressure at room temperature. The product was characterized to be 2,4-di(butoxycarbonylamino)-6-phenyl-1,3,5-triazine by $^1$H NMR, $^{13}$C NMR, active chlorine titration and TLC; (2.5 g, 90.5%).

EXAMPLE 24

PART A: Preparation of N,N,N',N'-Tetrachloroacetoguanamine

Acetoguanamine as a fine powder (12.5 grams) was mixed with 200 grams of deionized water and 27 grams of glacial acetic acid. The mixture was then cooled to about 13° C. and to it was added with stirring an aqueous solution containing 33.5 grams of sodium hypochlorite in approximately 5 percent concentration over a period of one hour. Additional acetic acid was occasionally added during the course of the reaction to keep the solution pH below 7. Thirty minutes after completion of NaOCl addition, the solid product was filtered off, washed with 700 ml of water, and dried under reduced pressure at room temperature to give a light yellow powder (22.65 g; 86% yield) characterized by $^1$H NMR, $^{13}$C NMR, and IR to be N,N,N',N'-tetrachloroacetoguanamine. Titration for active chlorine content gave a value of 14.64 mmol chlorine per gram of product, which corresponds to 96.2% of the theoretical value.

PART B: Preparation of N-Chlorinated 2,4-Di(butoxycarbonylamino)-6-methyl-1,3,5-triazines from N,N,N',N'-Tetrachloracetoguanamine and Butyl Chloroformate A mixture of 2.5 grams N,N,N',N'-tetrachloroacetoguanamine, 6 ml of n-butyl chloroformate, 20 ml of o-dichlorobenzene, and 30 milligrams of N,N-dimethylaminopyridine was heated under Argon with stirring for 24 hours at 68° C. The reaction solution was then cooled to room temperature and the excess reagent and o-dichlorobenzene were removed under reduced pressure.

The resulting yellow-orange solid (2.15 g) was found by $^1$H and $^{13}$C NMR, and by TLC analysis to be a mixture of unreacted, mono-butoxycarbonylamino (22%), and dibutoxycarbonylamino (16%) chloro acetoguanamines.

PART C: Preparation of 2,4-Di (butoxycarbonylamino)-6-methyl-1,3,5-triazine from N,N,N',N'-Tetrachloroacetoguanamine and Butyl Chloroformate A mixture of 2.5 g N,N,N',N'-tetrachloroacetoguanamine, 6 ml of n-butyl chloroformate, 20 ml of o-dichlorobenzene, and 0.12 g of Aliquat® 336 was heated under argon with stirring for 24 hours at 68° C. Upon cooling, 100 ml of hexane was added. The resulting precipitate was isolated, dried under reduced pressure (1.65 g, 56.3% yield), and identified by $^1$H NMR, $^{13}$C NMR, IR, TLC, and active chlorine analysis to be 2,4-di(butoxycarbonylamino)-6-methyl-1,3,5-triazine.

EXAMPLE 25

Preparation of N,N',N"-Triacetylmelamine from N,N',N"-Trichloromelamine and Acetyl Bromide A mixture of 1.38 grams of N,N',N"-trichloromelamine, 5.90 grams of acetyl bromide, and 40 ml of carbon tetrachloride was heated with stirring under Argon for 2 hours at 61° C. An evolution of a reddish-brown vapor (BrCl) was observed during the course of the reaction. After cooling, the orange solid was filtered, washed several time with CCl$_4$ and dried under reduced pressure at room temperature to afford a white powder (0.76 g, 50% yield).

The recovered product was characterized by $^1$H NMR, $^{13}$C NMR, and TLC analysis to be N,N',N"-triacetylmelamine, identical with the product of Example 14.

EXAMPLE 26

Debromination of N,N',N"-Tribromo-2,4,6-tri(methoxycarbonylamino)-1,3,5-Triazine with Hydrogen Chloride

Preparation of the 2,4,6-Tri(methoxycarbonylamino-1,3,5-Triazine Hydrochloride Salt A slurry of 0.98 grams of the material from Example 22, Part B, in 50 ml of carbon tetrachloride was cooled to 17° C. with an external water bath. This mixture was then saturated with anhydrous hydrogen chloride and allowed to stir for one hour. The solution color deepened during the course of the reaction from yellow to reddish orange. After one hour, the solid product was filtered, washed several times with CCl$_4$, and air dried overnight.

The product was a lightly yellow tinted powder (0.66 gms, 98% yield) characterized to be the HCl salt of 2,4,6-trimethoxycarbonylamino)-1,3,5-triazine by $^1$H and $^{13}$C NMR.

EXAMPLE 27

PART A: Preparation of N,N'-Dichloroacetoguanamine

A slurry of N,N,N',N'-tetrachloroacetoguanamine (5.3 g), acetoguanamine (2.5 g), deionized water (90 ml) and glacial acetic acid (0.2 ml) was heated with stirring at 50° C. under nitrogen for one hour. Upon cooling, the solid product was filtered off, washed with 140 ml of water, and dried under reduced pressure at room temperature to give a white power (7.4 g, 95% yield) characterized by $^1$H NMR, $^{13}$C NMR and IR to be N,N'-dichloroacetoguanamine. Titration for active chlorine content gave a value of 10.19 mmol chlorine per gram of product, which corresponds to 98.8% of the theoretical value. m.p. 186°–187° (dec).

PART B: Preparation of 2,4-Di(butoxycarbonylamino)-6-methyl-1,3,5-triazine from N,N'-Dichloroacetoguanamine and Butyl Chloroformate A mixture of 2.5 g N,N'-dichloroacetoguanamine, 8.3 ml n-butyl chloroformate, and 20 ml of o-dichlorobenzene was heated with stirring at 70° C. under Argon for five hours. Upon cooling, the insoluble solids were filtered off and washed with hexanes. The combined hexane/o-dichlorobenzene filtrate was concentrated under reduced pressure. The resulting colorless residue (2.3 g, 55% yield) was charactreized by IR, TLC, $^1$H NMR, $^{13}$C NMR, and active Cl analysis to be 2,4-di(butoxycarbonylamino)-6-methyl-1,3,5-triazine, identical with the product of Example 24, Part C.

EXAMPLE 28

Reaction of Trichloromelamine with Benzoyl Chloride Using 4-Dimethylamino pyridine (DMAP) as Catalyst To a stirring suspension of 1.15 g trichloromelamine in 30 ml CCl4 was added 4.2 g benzoyl chloride followed by 40 mg 4-dimethylaminopyridine. The reaction mixture was stirred at room temperature under Argon. After 0.5 hours the reaction mixture turned yellowish. A thin layer chromatographic analysis revealed the formation of tribenzoyl melamine as one of the products by comparison with an authentic sample of tribenzoyl melamine.

In a control experiment without the catalyst but under the same reaction conditions as above, formation of the tribenzoyl melamine was not observed after 0.5 hours. It is concluded from the above comparative experiments that 4-dimethylaminopyridine is an effective catalyst for the novel reaction of the invention.

EXAMPLE 29

Triazine Trisbutylcarbamate from Hexachloromelamine And Phosgene

About 5 ml of Phosgene was condensed by passing into 20 ml o-dichlorobenzene at $-10°$ C. in a two-neck flask equipped with a rubber septum, a magnetic stirring bar and a reflux condenser with a CaCl$_2$ drying tube. A solution of 1.67 gm hexachoromelamine in 10 ml o-dichlorobenzene was slowly added to the flask using a syringe under argon. After 15 minutes of stirring at $-10°$ C., the cooling bath was removed and the reaction mixture was stirred at room temperature for 2 hours. The reaction mixture was then heated in an oil bath to 110° C. and kept at this temperature for 3 hours. Heating was discontinued and the reaction mixture was allowed to cool to room temperature and then cooled to about 0° C. in an ice bath. After adding 10 ml of n-butanol the reaction mixture was stirred at room temperature for 2 hours. The reaction mixture was concentrated under reduced pressure by removing the volatiles and the residue was treated with 50 ml n-hexane. The precipitated white product was filtered and dried under reduced pressure to yield 1.95 gm of the product. TLC analysis of this product showed that triazine trisbutylcarbamate was formed as the major product, which was identical with the product obtained in Example 3.

EXAMPLE 30

Triazine Trisbutylcarbamate from Hexachloromelamine And Oxalyl Chloride 1.66 gm of hexachloromelamine was placed in a two-neck 100 ml flask equipped with a magnetic stirring bar, a reflux condenser, an argon inlet and a rubber septum. To it was added 10 ml o-dichlorobenzene and the mixture was cooled in an ice bath. 2 ml of oxalyl chloride was added with a syringe and the reaction mixture was stirred at about 0° C. for 1 hour. It was then heated to about 100° C. in an oil bath for nearly 16 hours. Heating was discontinued and the reaction flask cooled to about 0° C. 10 ml of n-butanol was added to the reaction flask and the reaction mixture was stirred at room temperature for 2 hours. Formation of triazine trisbutylcarbamate as the major product was confirmed by direct comparison with an authentic sample on a TLC plate. The reaction mixture was concentrated under reduced pressure and the residue treated with 50 ml n-hexane. The precipitated material was filtered off and dried under reduced pressure (1.8 gm). The product, triazine trisbutylcarbamate, formed in this reaction was identical with the product obtained in Example 3.

EXAMPLE 31

Triazine Trisbutylcarbamate from Trichloromelamine And Oxalyl Chloride

Following the procedure above for the reaction of hexachloromelamine with oxalyl chloride, 2.29 gm of trichloromelamine was allowed to react with 4 ml of oxalyl chloride in 20 ml ortho-dichlorobenzene. TLC analysis of the crude product obtained after treatment of the reaction mixture with n-butanol, confirmed the formation of triazine trisbutylcarbamate.

EXAMPLE 32

2,4-Di(butoxycarbonylamino)-6-phenyl-1,3,5-triazine from N,N,N'-Trichlorobenzoguanamine And Oxalyl Chloride 2.9 gm of N,N,N'-tricholorobenzoguanamine, prepared in Example 23, Part A, was placed in a 3-neck 100 ml flask equipped with a reflux condenser, a magnetic stirring bar, an argon inlet, a glass stopper and a rubber septum. To the flask was added 25 ml of o-dichlorobenzene followed by dropwise addition with a syringe of 6.35 gm of oxalyl chloride. The reaction mixture was stirred for 0.5 hour at room temperature and then heated in an oil bath at 50°-55° C. for 20 hours. Heating was discontinued and the reaction mixture was cooled to about $-10°$ C. n-Butanol (20 ml) was added to the reaction flask. The cooling bath was removed after 10 minutes and the reaction mixture stirred at room temperature for 2 hours. TLC analysis of the reaction mixture showed a major spot with an identical R$_f$ with 2,4-di(butoxycarbonylamino)-6-phenyl-1,3,5-triazine prepared in Example 23, Part B. Formation of 2,4-di(butoxycarbonylamino)-6-phenyl 1,3,5-triazine was further confirmed by mass spectroscopy.

EXAMPLE 33

Triazine Trisbutylcarbamate And Triazine Trismethylcarbamate From Hexachloromelamine And Trichloromethyl Chloroformate (Diphosgene)

To a stirring solution of 1.65 gm of hexachloromelamine in 20 ml ortho-dichlorobenzene, in a two-neck flask equipped with a reflux condenser, a rubber septum, a magnetic stirring bar and an argon inlet, was added 4.0 gm of trichloromethyl chloroformate dropwise with a syringe. The rubber septum was replaced by a glass stopper and the reaction mixture was heated to 60°-65° C. in an oil bath for 6 hours. Then the temperature was increased to 110° C. for about 20 hours. The reaction mixture was cooled to room temperature and divided into two equal Parts "A" and "B".

Part "A" was added to a two-neck flask containing 20 ml of n-butanol at about 0° C. under argon while stirring. The reaction mixture was then stirred at room temperature for 2 hours. TLC analysis of the reaction mixture confirmed the formation of triazine trisbutylcarbamate when directly compared with an authentic sample prepared in Example 3. Volatiles were removed under reduced pressure to leave behind 1.0 gm of crude product.

Part "B" was similarly treated with 20 ml of methanol at about 0° C. to give 700 mg of crude product containing mainly triazine trismethylcarbamate confirmed by direct comparison on TLC with an authentic sample prepared in Example 2.

EXAMPLE 34

Triazine Trisbutylcarbamate From Hexachloromelanine And Bis(trichloromethyl) Carbonate (Triphosgene)

A mixture of 1.66 gm of hexachloromelamine, 1.78 gm of triphosgene and 10 ml ortho-dichlorobenzene was heated at 60° C. in an oil bath with stirring under argon in a two-neck flask equipped with a reflux condenser and a glass stopper. After 24 hours at 60° C., the temperature of the oil bath was raised to 100° C. for 24 hours and then the reaction mixture was slowly cooled down to about 0° C. n-Butanol (10 ml) was added to the cooled reaction mixture, which was then brought to room temperature and stirred for 4 hours. The reaction mixture was then diluted with 20 ml $CH_2Cl_2$ and filtered. The filtrate showed a major spot corresponding to triazine trisbutylcarbamate on TLC, confirmed by direct comparison with an authentic sample.

EXAMPLE 35

Reaction of N,N',N''-Trichloromelamine With Trichloromethyl Chloroformate (Diphosgene)

To a stirring suspension of 2.3 gm of N,N',N''-trichloromelamine in 25 ml ortho-dichlorobenzene in a two-neck, flask equipped with a reflux condenser, an argon inlet, a magnetic stirring bar and a rubber septum, was added 7.9 gm of trichloromethyl chloroformate dropwise with a syringe. The reaction flask was heated in an oil bath at 60°–65° C. for 20 hours. It was then cooled to room temperature and diluted with 50 ml n-hexane. The contents were stirred at room temperature for 2 hours. The precipitate was filtered, washed with n-hexane and dried under reduced pressure to give 2.32 gm of product as indicated by TLC.

EXAMPLE 36

Reaction of N,N',N''-Trichloromelamine with Bis(trichloromethyl) carbonate (Triphosgene)

A mixture of 2.29 gm of N,N',N''-trichloromelamine, 5.94 gm of bis(trichloromethyl)carbonate (triphosgene) and 30 ml of ortho-dichlorobenzene was heated at 60°–65° C. (oil bath) under stirring in a two-neck flask equipped with a magnetic stirring bar, a reflux condenser, an argon inlet and a glass stopper. Formation of chlorine gas was observed. The reaction mixture was heated at 60°–65° C. for 24 hours. It was then cooled to room temperature and diluted with 50 ml n-hexane. The reaction mixture was then stirred at room temperature for 2 hours. The precipitate was filtered, the residue washed with 50 ml n-hexane and dried under reduced pressure to give 2.3 gm of product as indicated by TLC.

EXAMPLE 37

2,4-Di(butoxycarbonylamino)-6-phenyl-1,3,5-triazine From N,N,N'-Trichlorobenzoguanamine And Trichloromethyl Chloroformate (Diphosgene)

1.45 gm of N,N,N'-trichlorobenzoguanamine (prepared in Example 23 Part A) was placed in a two-neck 100 ml flask equipped with a magnetic stirring bar, a reflux condenser, an argon inlet and a rubber septum. To the reaction flask was added 15.0 ml ortho-dichlorobenzene followed by dropwise addition of trichloromethyl chloroformate at about 0° C. The cooling bath was removed and the reaction mixture was heated at 50° C. in an oil bath for 4 hours. The temperature of the oil bath was increased to 100° C. and the reaction mixture was heated at this temperature for 24 hours. The heating was discontinued and the reaction mixture was allowed to cool to room temperature. It was then cooled to about 0° C. in an ice bath and 10 ml n-butanol was added to it. The contents were stirred at about 0° C. for 10 minutes and then the stirring was continued for 2 hours at room temperature. Analysis of the product by TLC confirmed the formation of 2,4-di(butoxycarbonylamino)-6-phenyl-1,3,5-triazine.

EXAMPLE 38

2,4-Di(butoxycarbonylamino)-6-phenyl 1,3,5-triazine From N,N,N'-Trichlorobenzoguanamine And Bis(trichloromethyl) Carbonate (Triphosgene)

In a two-neck flask, equipped with a reflux condenser, an argon inlet, a magnetic stirring bar and a rubber septum, was placed 1.45 gm of N,N,N'-trichlorobenzoguanamine (prepared in Example 23 Part A) and 1.78 gm of triphosgene. To the reaction mixture was added 10 ml of ortho-dichlorobenzene and the contents were heated in an oil bath at 60° C. for 24 hours. The temperature of the oil bath was increased to 100° C. and the reaction mixture was heated at this temperature for additional 24 hours. The heating was discontinued and the oil bath was replaced by an ice bath. n-Butanol (10 ml) was added dropwise to the reaction mixture at about 0° C. and the reaction mixture was stirred first at about 0° C. for 10 minutes and then at room temperature for 4 hours. TLC analysis of the reaction mixture confirmed the formation of 2,4-di(butoxycarbonylamino)-6-phenyl 1,3,5-triazine.

EXAMPLE 39

2,4-Di(butoxycarbonylamino)-6-phenyl-1,3,5-triazine from N,N,N'-Trichlorobenzoguanamine and Phosgene In a two-neck 100 ml flask equipped with a magnetic stirring bar, a reflux condenser, an argon inlet and a rubber septum was placed 1.45 gm of N,N,N'-trichlorobenzoguanamine (prepared in Example 23 part A). To the reaction flask was added 15.0 ml ortho-dichlorobenzene at about 0° C. followed by dropwise addition of 20 ml of 20% phosgene solution in toluene. The reaction mixture was stirred at about 0° C. for 1 hour and 4 hours at room temperature. The reaction mixture was then heated in an oil bath at approximately 110° C. for 24 hours. The reaction mixture was then cooled to about 0° C. and 10 ml n-butanol was added. The contents were stirred at about 0° C. for 1 hour and at room temperature for 2 hours. TLC of the reaction mixture confirmed the formation of 2,4-di(butoxycarbonylamino)-6-phenyl-1,3,5-triazine.

EXAMPLE 40

Reaction of Hexachloromelamine with Oxalyl Chloride followed by reaction with 4-Amino-2,2,6,6-tetramethyl Piperidine 1.66 gm of hexachloromelamine was treated with 2 ml of oxalyl chloride in 10 ml of ortho-dichlorobenzene following the procedure described in Example 30. After heating for 16 hours at 100° C., the reaction mixture was cooled to 0° C. 4 ml of 4-amino-2,2,6,6-tetramethyl piperidine was then added dropwise with stirring. The contents were stirred at about 0° C. for 1 hour and then at room temperature for two hours. The reaction mixture was diluted with 50 ml n-hexane. The precipitated material was filtered, washed with 100 ml n-hexane and dried. TLC of the product then obtained showed a major spot having an $R_f$ identical with the product obtained from the reaction of triazine trisphenylcarbamate with 4-amino-2,2,6,6-tetramethyl piperidine described in Example 19.

Although the present invention has been described with reference to certain preferred embodiments, it is apparent that modifications and variations thereof may be made by those skilled in the art without departing from the scope of this invention as defined by the appended claims.

What is claimed is

1. A process for preparing an acid amide from a haloaminotriazine and an acid halide comprising: contacting said haloaminotriazine with said acid halide at a temperature and for a length of time sufficient to produce said acid amide, wherein the haloaminotriazine is selected from the group consisting of:

(i) a halogenated melamine represented by the formula (I):

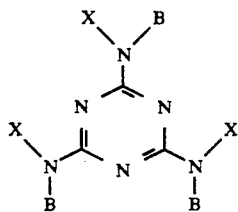

wherein each X group is the same or different and is selected from the group consisting of hydrogen, chloro, bromo, iodo and fluoro groups, provided that at least one X group is a halogen; and wherein each B group is the same or different and is selected from the group consisting of hydrogen, chloro, bromo, iodo, fluoro, alkyl, alkylenealkoxy, triazino, pyrimidino, pyridino, imidazolo, tetrazolo, silyl, cyano, perfluoroalkyl, perfluoroaryl, and perfluoroaralkyl groups;

(ii) a halogenated guanamine represented by the formula (II):

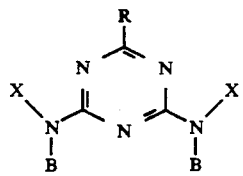

wherein X and B are the same as described above; and wherein R is selected from the group consisting of linear alkyl of 1 to 20 carbon atoms, cyclic or branched alkyl of 3 to 20 carbon atoms, alkenyl of 2 to 20 carbon atoms, aryl of 6 to 20 carbon atoms, aralkyl of 7 to 20 carbon atoms, alkoxy of 1 to 20 carbon atoms, aryloxy of 6 to 20 carbon atoms, alkylthio of 1 to 20 carbon atoms, arylthio of 6 to 20 carbon atoms, alkylamino of 1 to 20 carbon atoms, dialkylamino of 2 to 40 carbon atoms, morpholino, piperidino, pyrrolidino, aminotriazino, alkylaminotriazino, aminoalkylaminotriazino, hydrogen, chloro, bromo, iodo, fluoro, perfluoroalkyl, perfluoroaryl, and perfluoroaralkyl groups; and (iii) a mixture of any of (i) and (ii).

2. The process for preparing an acid amide from a haloaminotriazine and an acid halide as recited in claim 1 wherein the haloaminotriazine is selected from the group consisting of monohalomelamine, dihalomelamine, trihalomelamine, tetrahalomelamine, pentahalomelamine, hexahalomelamine, haloacetoguanamines, halobenzoguanamines, halocyclohexylcarboguanamines, isomers thereof, and mixtures thereof.

3. The process for preparing an acid amide from a haloaminotriazine and an acid halide as recited in claim 2 wherein the haloaminotriazine is N,N',N''-trichloromelamine or N,N,N',N',N'',N''-hexachloromelamine.

4. The process for preparing an acid amide from a haloaminotriazine and an acid halide as recited in claim 2 wherein the haloaminotriazine is selected from the group consisting of di-, tri-, or tetrachloroacetoguanamine, di-, tri-, or tetrachlorobenzoguanamine, di-, tri-, or tetrachlorocyclohexylcarboguanamine, and mixtures thereof.

5. The process for preparing an acid amide from a haloaminotriazine and an acid halide as recited in claim 1 wherein the by-product is molecular halogen in the substantial absence of hydrogen halide.

6. The process for preparing an acid amide from a haloaminotriazine and an acid halide as recited in claim 1 wherein the acid halide is represented by the formula:

$$Z+Y—X)_M$$

wherein M is at least 1; and when M is at least 2, each +Y—X) group is the same or different;

X is a halogen selected from the group consisting of chloro, bromo, iodo, fluoro, and mixtures thereof;

Y in each +Y—X) group is the same or different and each is independently selected from the group consisting of the following functionalities represented by the formulae:

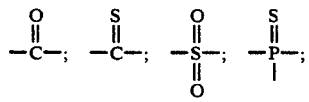

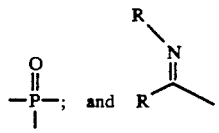

wherein each R is independently an alkyl, aryl, or an alkoxy group; and

Z is an M-functional anchor selected from the group consisting of hydrogen, chloro, bromo, iodo, fluoro, vinyl, alkyl of 1 to 20 carbon atoms, alkylene of 1 to 20 carbon atoms, arylene of 6 to 20 carbon carbon atoms, haloalkyl of 1 to 20 carbon atoms, aryl of 6 to 20 carbon atoms, haloaryl of 6 to 20 carbon atoms, aralkyl of 7 to 20 carbon atoms, haloaralkyl of 7 to 20 carbon atoms, acyl of 2 to 20 carbon atoms, haloacyl of 2 to 20 carbon atoms, halocarbonyl, alkoxycarbonyl of 2 to 20 carbon atoms, alkylthiocarbonyl of 2 to 20 carbon atoms, haloalkoxy of 2 to 20 carbon atoms, aminocarbonyl, alkylaminocarbonyl of 2 to 20 carbon atoms, dialkylaminocarbonyl of 3 to 20 carbon atoms, alkenylaminocarbonyl of 4 to 20 carbon atoms, dialkenylaminocarbonyl of 7 to 40 carbon atoms, alkylalkenylaminocarbonyl of 5 to 20 carbon atoms, perfluoroalkyl of 1 to 20 carbon atoms, perfluoroaryl of 6 to 20 carbon atoms, perfluoroaralkyl of 7 to 20 carbon atoms, haloalkyl of 1 to 20 carbon atoms, alkoxycarbonylalkyl of 3 to 20 carbon atoms, cyanoalkyl of 2 to 20 carbon atoms, formylalkyl of 2 to 20 carbon atoms, ketoalkyl of 3 to 20 carbon atoms, trialkoxysilylalkyl of 4 to 20 carbon atoms, dialkylaminoalkyl of 3 to 20 carbon atoms, alkoxyalkyl of 2 to 20 carbon atoms, alkoxy of 1 to 20 carbon atoms, aryloxy of 6 to 20 carbon atoms, alkenyloxy of 3 to 20 carbon atoms, aklylenedioxy of 2 to 20 carbon atoms, arylenedioxy of 6 to 20 carbon atoms, N,N-dialkylamino of 2 to 40 carbon atoms, N,N-dialkenylamino of 6 to 40 carbon atoms, N,N-diarylamino of 12 to 40 carbon atoms, N,N-alkylalkenylamino of 4 to 40 carbon atoms, N,N-alkylarylamino of 7 to 20 carbon atoms, N,N-alkenylarylamino of 9 to 20 carbon atoms, aziridino, azetidino, pyrrolidino, piperidino, morpholino, alkylmercapto of 1 to 20 carbon atoms, alkenylmercapto of 3 to 20 carbon atoms, and arylmercapto of 6 to 20 carbon atoms.

7. The process for preparing an acid amide from a haloaminotriazine and an acid halide as recited in claim 6 wherein the acid halide is selected from the group consisting of alkyl chloroformates, aryl chloroformates, acyl chlorides, haloalkylcarbonyl chlorides, acryloyl chlorides, carbamoyl chlorides aklylene bis acid chlorides, arylene bis acid chlorides, alkylene bis chloroformates, and phosgene.

8. The process for preparing an acid amide from a haloaminotriazine and an acid halide as recited in claim 7 wherein the acid halide is selected from the group consisting of the following compounds represented by the formulae:

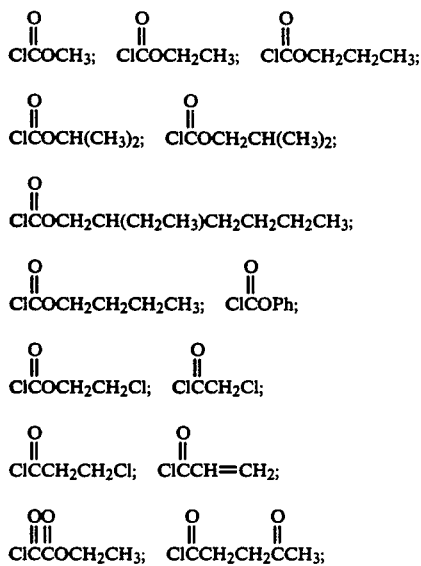

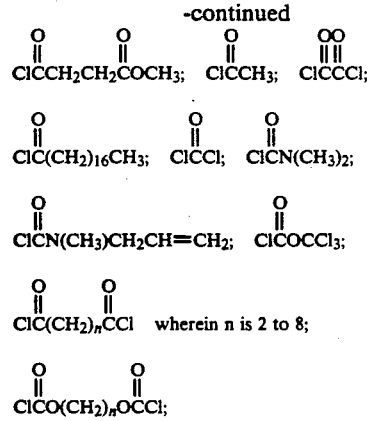

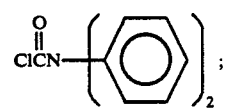 wherein n is 2 to 8;

wherein n is 2 to 8;

$$\underset{ClCN}{\overset{O}{\|}}{-}{\left(\!\!\underset{}{\bigcirc}\!\!\right)}_{2};$$

and $$\underset{ClCN}{\overset{O}{\|}}{+}CH_2CH{=}CH_2)_2.$$

9. The process for preparing an acid amide from a haloaminotriazine and an acid halide as recited in claim 8 wherein the acid halide is selected from the group consisting of methylchloroformate, n-butyl chloroformate, phenyl chloroformate, 2-chloroethyl chloroformate, ethyl chloroformate, propyl chloroformate, isopropyl chloroformate, isobutyl chloroformate, 2-ethylhexyl chloroformate, chloroacetyl chloride, 4-chlorobutyryl chloride, acryloyl chloride, methacryloyl chloride, oxalyl chloride, ethyl oxalyl chloride, acetyl chloride, stearoyl chloride, and phosgene.

10. The process for preparing an acid amide from a haloaminotriazine and an acid halide as recited in claim 9 wherein the haloaminotriazine is selected from the group consisting of N,N',N"-trichloromelamine N,N,N',N',N", N" - hexachloromelamine, N,N,N',N'-tetrachloroacetoguanamine, N,N,N',N'-tetrachlorobenzoguanamine, N,N,N',N'-tetrachlorocyclohexylcarboguanamine, and mixtures thereof.

11. The process for preparing an acid amide from a haloaminotriazine and an acid halide as recited in claim 1 wherein the reaction mixture further comprises a catalyst selected from the group consisting of trialkyl phosphines, triaryl phosphines, quaternary ammonium halides, monomeric 4-dialkylaminopyridine, and a polymeric 4-dialkylamino pyridine derivative.

12. A process for producing a triazine tris-acid amide from melamine via trihalomelamine comprising:
(a) contacting said melamine with an halogen to produce hexahalomelamine;
(b) contacting melamine with hexahalomelamine to produce trihalomelamine;
(c) contacting said trihalomelamine with an acid halide at a temperature and for a length of time sufficient to produce triazine tris-acid amide as a product and halogen as a by-product; and
(d) recycling the halogen by-product into step (a) to halogenate melamine to hexahalomelamine.

13. A process for producing a triazine tris-acid amide from melamine via hexahalomelamine comprising:

(I) contacting said melamine with a halogen to produce hexahalomelamine;

(II) contacting said hexahalomelamine with an acid halide at a temperature and for a length of time sufficient to produce triazine N,N',N''- trihalo tris-acid amide as an intermediate product and halogen as a by-product;

(III) contacting the triazine N,N',N''-trihalo tris-acid amide intermediate of step (II) with hydrogen halide to produce triazine tris-acid amide as a final product and additional halogen as a by-product; and (IV) recycling the halogen by-product of steps (II) and (III) into step (I) to halogenate melamine to hexahalomelamine.

* * * * *